United States Patent
Salvemini (12)

(10) Patent No.: US 6,180,620 B1
(45) Date of Patent: Jan. 30, 2001

(54) ANALGESIC METHODS USING SYNTHETIC CATALYSTS FOR THE DISMUTATION OF SUPEROXIDE RADICALS

(75) Inventor: Daniela Salvemini, Creve Couer, MO (US)

(73) Assignee: G.D. Searle & Co., Chicago, IL (US)

(*) Notice: Under 35 U.S.C. 154(b), the term of this patent shall be extended for 0 days.

(21) Appl. No.: 09/057,831

(22) Filed: Apr. 9, 1998

Related U.S. Application Data

(60) Provisional application No. 60/050,402, filed on Jun. 20, 1997.

(51) Int. Cl.[7] .................................................. A61K 31/555
(52) U.S. Cl. ............................................................ 514/184
(58) Field of Search ............................................. 514/184

(56) References Cited

U.S. PATENT DOCUMENTS

| | | | |
|---|---|---|---|
| 4,877,561 | 10/1989 | Iga et al. | 264/4.3 |
| 4,999,347 | 3/1991 | Sorenson | 514/159 |
| 5,541,174 | 7/1996 | Sorenson | 514/186 |
| 5,637,578 | 6/1997 | Riley et al. | 514/186 |

FOREIGN PATENT DOCUMENTS

| | | |
|---|---|---|
| 0524161 A1 | 2/1992 | (EP) . |
| WO 94/15925 | 1/1994 | (WO) . |
| WO 96/39396 | 12/1996 | (WO) . |

OTHER PUBLICATIONS

Derwent Abstract (WPI Acc. No. 95–232188/19 9531) of Chinese Patent CN 108806A to Guo et al. Jun. 22, 1994.

Bert C. Del Villano, et al., "Elevated Superoxide Dismutase in Black Alcoholics," Feb. 29, 1980, (Science, vol. 207) pp. 991–993.

E. Lengfelder, et al., "Superoxide Dismutation by Low Molecular Weight Cu–Complexes," 1981, (Bull Europ Physiopath. Resp.) pp. 73–80.

Joseph L. Joyave, et al., "Alteration of Chemically Induced Hepatotoxicity by Copper (II) (3,5–Diisopropylsalicylate)$_2$," 1985, (Biochemical Pharmacology, vol. 34, No. 21) pp. 3915–3919.

"Modified Superoxide Dismutase as Inflammation Inhibitor and Others," 1989, (Chemical Abstracts, vol. 111, No. 15) p. 353.

Shigeru Okuyama, et al., "Copper Complexes of Non–steroidal Antiinflammatory agents: Analgesic Activity and Possible Opioid Receptor Activation$_1$," 1987, (Agents and Actions, vol. 21, 1/2) pp. 130–144.

Rina Varsano et al., "Superoxide Dismutase Activity in Morphine– and Meperidine– Addicted Mice and Their Response to Paraquat Poisoning," 1992, (FEBS) pp. S54–S59.

Susan T. Shuff, et al., "Stable Superoxide Dismutase (SOD)–Mimetic Ternary Human Serum Albumin–Cu(II)(3, 5–Diisopropylsalicylate)$_4$ Complexes in Tissue Distribution of the Binary Complex," 1992, (Biochemical Pharmacology, vol. 43, No. 7) pp. 1601–1612.

A. Kohut, et al., "Effect of Allopurinol and Superoxide Dismutase on Indomethacin–Induced Gastric Lesions in the Rat," 1993, (Physiol. Res. 42 pp. 273–276.*

Y. Lin, et al., "Use of Superoxide Dismutase (SOD in Patients with Temporomandibular Joint Dysfunction—a Preliminary Study," 1994, (Int. J. Oral Maxillofac. Surg.), pp. 428–429.*

Gregory Elmer, et al., "Transgenic Superoxide Dismutase Mice Differ in Opioid–Induced Analgesia," 1995 (European Journal of Pharmacology), pp. 227–232.*

N. Goldstein, et al., "Exogenous Gaseous Superoxide Potentiates the Antinociceptive Effect of Opioid Analgesic Agents," 1996 (vol. 45), pp. 473–478.*

M. Tal, "A Novel Antioxidant Alleviates heat Hyperalgesia in Rats with an Experimental Painful Peripheral Neuropathy," 1996 (NeuroReport 7), pp. 1382–1384.*

R. Li, "Synthesis and Pharmacological Activities of 1,1–Dialkyl–4 (3–Bromopropoionyl) Piperazinium Bromides," 1996 (Acta Pharmacetica Sinica), pp. 757–760.*

The Merck Index, Twelfth Edition. S. Budavari, editor. Merck & Co., Inc., Whitehouse Station, NJ, 1996. pp. 1540–1541, monograph 9177.

* cited by examiner

*Primary Examiner*—Kathleen K. Fonda
(74) *Attorney, Agent, or Firm*—Senniger, Powers, Leavitt & Roedel

(57) ABSTRACT

Synthetic low molecular weight catalysts for the dismutation of superoxide are potent analgesics that are effective in elevating the pain threshold in hyperalgesic conditions such as arthritis, and also operate to prevent or reverse tolerance to opioid analgesics.

9 Claims, 4 Drawing Sheets

ANALGESIC METHODS USING SYNTHETIC CATALYSTS FOR THE DISMUTATION OF SUPEROXIDE RADICALS

This application claims the benefit of U.S. Provisional Application No. 60/050,402, filed Jun. 20, 1997.

TECHNICAL FIELD

This invention relates to the treatment of humans and lower animals in pain management: to prevent or relieve pain, to prevent or reverse tolerance to opioid analgesics and hyperalgesia associated with prolonged opioid treatment, and to prevent or reduce symptoms of opioid withdrawal and related withdrawal syndromes.

BACKGROUND ART

Numerous analgesics are known to medical science. Many analgesics fall into one of two large categories—nonsteroidal analgesic/anti-inflammatory drugs (NSAIDs) and opioids. NSAIDs operate by inhibiting cyclooxygenase enzymes and thereby the synthesis of prostaglandins. Prostaglandins sensitize pain receptors, lowering the pain threshold and making normal stimuli, such as touch and stretch sensations, painful. NSAIDs can be quite effective at returning the lowered pain threshold to normal but do not elevate the pain threshold.

A second class of pain relievers, opioids or opioids, operate by mimicking natural peptides such as enkephalins and endorphins to stimulate one or more of the $\mu$-, $\delta$- and $\kappa$-receptor systems in the nervous system. Opioids elevate the pain threshold so that normally painful stimuli are perceived as less painful or even euphoric. Opioids are commonly used in the clinical management of severe pain, including chronic severe pain of the kind experienced by cancer patients.

Capsaicin and its derivatives operate by depleting local stores of substance P, a neuropeptide involved in the transmission of pain impulses and are used in several OTC analgesic products.

Each of these classes of compounds has inherent problems and limitations. The opioid analgesics are antagonized by analogous N-allyl compounds such as naloxone; the NSAID analgesics are not. NSAIDs that are nonselective for the cyclooxygenase 2 produced in inflammation (COX-2) also inhibit constitutive cyclooxygenase 1 (COX-1), causing undesirable damage to the gastric mucosa. They have limited effectiveness as analgesics in lowering an elevated threshold to normal and are generally used for mild to moderate pain. They are also ineffective drugs for elevation of the pain threshold above normal levels, which prevents their use in pain such as surgical pain where an underlying pathological condition has not elevated the pain threshold.

Opioids have problems with tolerance and dependency, so that over a course of therapy increasing dosages of compound are required to achieve the same level of analgesia, and cessation of opioid administration when analgesia is no longer needed elicits a withdrawal syndrome with unpleasant and potentially serious symptoms. The dependency and withdrawal syndrome both make it difficult for the clinician to discontinue opioid therapy even when the opioids are no longer effective in relieving pain because of the development of tolerance. Narcotic induced hyperalgesia (NIH) can also develop in association with tolerance to the opioids. All of these factors limit the usefulness of opioids in the management of chronic severe pain, despite their potency.

No adequate strategy has been devised to overcome the development of opioid tolerance and provide an ongoing approach to the management of chronic severe pain. Mechanisms of tolerance are not well understood but are known to involve the NMDA receptor, since the NMDA receptor antagonist MK-801 has been shown in rats to prevent morphine tolerance. NMDA stimulates nitric oxide synthase (NOS) and NOS has been observed histochemically in tissues that contain opioid receptors and are important in the pain response, such as the amygdala, cortical gray matter, and the substantia gelatinosa of the spinal cord. Nonselective NOS inhibitors such as NG-nitroarginine prevent and reverse morphine tolerance. However, nonselective inhibition of NOS is associated with a vast array of undesirable side effects, including hypertension, increased platelet and white blood cell reactivity, decreased cerebral blood flow, and gastrointestinal and renal toxicity.

Capsaicin and some of its derivatives, in addition to producing analgesia, also elicit a burning sensation. This effect is responsible for the pungency of hot peppers (Capscum spp.) and limits the applicability of many members of this series of compounds.

For these and other reasons, a continuing need exists for new high potency analgesics. A need also exists for methods for reversing tolerance to opioid analgesics so that patients who require these drugs for pain over extended periods can do so without loss of potency and efficacy.

One object of this invention is to provide new methods for the prevention and relief of mild to severe pain by identifying a new biological activity of a class of synthetic catalyst compounds, and by specifying a new indication for those compounds.

It is another object of this invention to provide methods for preventing and reversing tolerance to opioid analgesics by identifying another new biological activity of that class of catalysts and another new indication for those compounds.

These and other objects of the invention will be evident from the following disclosure.

DISCLOSURE OF THE INVENTION

Figure 1:
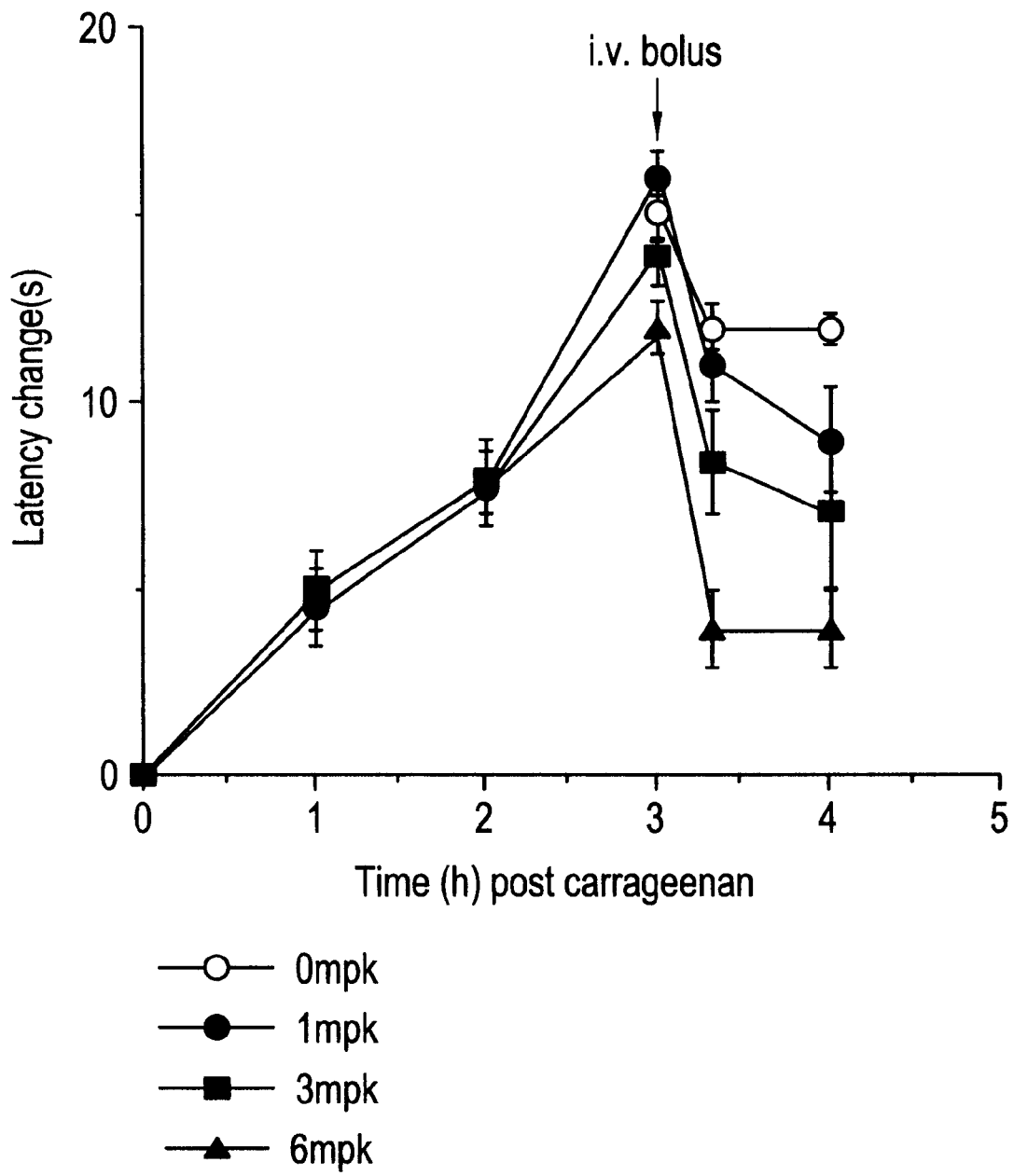
FIG. 1 is a graph depicting the results of a study on the inhibition of carrageenan-induced hyperalgesia by intravenously injected SC-72325. The drug was given at 3 hours post carrageenan injection.

This invention is based upon surprising discoveries involving certain organometallic complexes designed as synthetic catalysts for use in the body. These catalysts have been designed as synthetic replacements for or adjuncts to the naturally occurring enzyme superoxide dismutase (SOD).

Naturally occurring SOD scavenges and eliminates the toxicity of free superoxide radicals ($O_2^-$.) liberated by certain metabolic reactions. Although these free radicals play a major (and deleterious) role in the inflammatory response and other toxic reactions to injury, neither superoxide nor SOD has been known to be directly involved in pain perception. In addition, SOD has a very short biological half-life, on the order of seconds or minutes rather than hours, so it would be considered unsuitable for treatment of conditions in which increased dismutation of superoxide radicals would be desirable over periods of from minutes to days.

Dismutation of superoxide radicals is catalyzed by a coordinated transition metal ion. In the natural SOD enzyme, the metal is manganese, copper or zinc and the coordination complex is a conventional protein structure. Synthetic SOD catalysts also use transition metals, complexed with low molecular weight organic ligands, generally polydentate N-containing macrocycles. These molecules have been designed to be highly efficient and to overcome the pharmacokinetic disadvantages of natural SOD enzyme. The $k_{cat}$ of some of these compounds is as high as about $10^9$ (see Example 165), indicating extraordinary catalytic efficiency, as effective as the natural enzyme and approaching the theoretical rate at which diffusion can deliver free radical substrate to the catalyst under biological conditions. They also have oil:water partition coefficients ($_{log}P$) that provide excellent bioavailability, and stability in the body on the order of hours to days. Their small size and low molecular weight makes it possible for the synthetic catalysts to cross membrane barriers that restrict movement of natural SOD, and their non-protein structure reduces the risk of allergic reactions that have been a problem with the administration of protein-based recombinant SOD. Finally, natural SOD produces hydrogen peroxide in the process of dismutating superoxide, yet hydrogen peroxide inhibits natural SOD, effectively self-limiting the efficacy of the natural compound. In contrast, synthetic small-molecule SOD catalysts are not susceptible to the action of hydrogen peroxide and thus retain their effectiveness.

Synthetic SOD catalysts have been proposed in the past for the treatment and prevention of inflammation, ischemia-reperfusion injury, and similar conditions where tissue damage is mediated by levels of free superoxide radicals that overwhelm natural SOD, but they have not been proposed for use as analgesics in the treatment of pain.

It has now been discovered that synthetic SOD catalysts are highly effective as analgesics to prevent or provide relief from pain in conditions in which the pain threshold is elevated. It has also been discovered that these same compounds are effective in preventing or reversing tolerance to opioid analgesics, that are used to elevate the pain threshold above normal levels.

No known mechanism accounts for the analgesic properties of these compounds. However, the data shown in the examples illustrate that these compounds can be as effective as morphine in preventing and relieving certain kinds of pain. Y. Lin et al., Int. J. Maxillofac. Surg. 23:428–429 (1994) reported the use of intra-articular injections of human Cu/Zn superoxide dismutase as a nonsteroidal anti-inflammatory in the treatment of temporomandibular joint dysfunction. Positive response in terms of mandibular movement and pain was observed in 83% of patients. The authors note that the results "are remarkable because SOD has been studied and shown to exert no peripheral or central analgesic effect." They attribute the reduction in pain to the reduction in tissue injury and inflammation associated with TMJ dysfunction.

Similarly, no known mechanism accounts for the ability of these compounds to prevent or reverse tolerance to opioids. G. I. Elmer et al., Euro. J. Pharmacol. 283 (1995) 227–232, reported that transgenic mice expressing the human Cu/Zn superoxide dismutase gene had an increase in μ-opioid receptor concentration in dopaminergic related tissues and the central grey area of the CNS, which was associated with a dose-related increased sensitivity to μ-receptor agonists such as morphine. At the same time the authors also observed conflicting effects of transgenic SOD on δ-receptor agonists (mice heterozygous for the transgene were more sensitive than homozygotes, which were more sensitive than untransformed mice) and observed no effect of transgenic SOD on κ-receptor agonists.

Superoxide dismutase activity is known to play a critical role in regulating the redox state of the cell, as reported by J. L. Cadet, Int. J. Neurosci. 40, 13 (1988). This in turn is reported by Marzullo and Hine, Science 208, 1171 (1980) to significantly affect in vitro μ- and δ-opioid binding.

MODES FOR CARRYING OUT THE INVENTION

In particular, this invention provides a method of producing analgesia in a human or lower mammal patient, comprising administering to the patient an analgesic amount of a functional synthetic catalyst for the dismutation of superoxide radicals. Based on the data obtained, it is reasonable to expect that any superoxide dismutase catalyst will be effective in the practice of this invention. A preferred synthetic catalyst is a coordination complex of transition metal with an organic ligand. Preferred transition metals are copper, manganese and zinc. Manganese is most preferred. In general, the organic ligand is a N-containing macrocycle, and most preferred ligands are selected from the group consisting of compounds of the formula

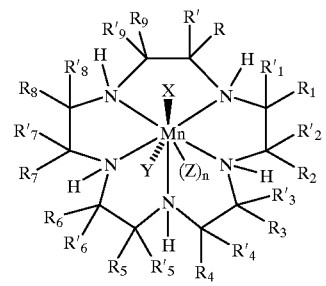

wherein R, R', $R_1$, $R'_1$, $R_2$, $R'_2$, $R_3$, $R'_3$, $R_4$, $R'_4$, $R'_5$, $R_6$, $R'_6$, $R_7$, $R'_7$, $R_8$, $R'_8$, $R_9$ and $R'_9$ independently are selected from the group consisting of hydrogen and substituted or unsubstituted alkyl, alkenyl, alkynyl, cycloalkyl, cycloalkenyl, cycloalkylalkyl, cycloalkylcycloalkyl, alkylcycloalkyl, cycloalkenylalkyl, alkenylcycloalkyl, alkylcycloalkenyl, alkenylcycloalkenyl, heterocyclic, aryl and aralkyl radicals, or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$, together with the carbon atoms to which they are attached independently form a substituted or unsubstituted saturated, partially saturated or unsaturated cyclic ring structure having 3 to 20 carbon atoms; or R or R', $R_1$ or $R'_1$, $R_2$ or $R'_2$, $R_3$ or $R'_3$ and $R_4$ or $R'_4$, $R_5$ or $R'_5$ and $R_6$ or $R'_6$, $R_7$ or $R'_7$, and $R_8$ or $R'_8$, and $R_9$ or $R'_9$, together with the carbon atoms to which they are attached independently form a substituted or unsubstituted nitrogen-containing heterocycle having 2 to 20 carbon atoms provided that when the nitrogen containing heterocycle is an aromatic heterocycle that does not have a hydrogen attached to the nitrogen, the hydrogen attached to the nitrogen in the macrocycle and the R groups attached to the same carbon atoms of the macrocycle are absent; R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$ and $R_9$ and $R'_9$, together with the carbon atom to which they are attached independently form a substituted or unsubstituted saturated, partially saturated or unsaturated ring structure having 3 to 20 carbon atoms; or two of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ attached to different carbon atoms of the macrocycle are bound to form a strap structure of the formula

wherein w, x, y and z independently are integers from 0 to 10 and M, L and J are independently selected from the group consisting of alkyl, alkenyl, alkynyl, cycloalkyl, aryl, heteroaryl, alkaryl, alkheteroaryl, aza, amido, ammonium, thio, sulfonyl, sulfinyl, sulfonamido, phosphonyl, phosphinyl, phosphino, phosphonium, keto, ester, carbamyl, ureido, thiocarbonyl, borate, borane, boraza, silyl, siloxy and silaza radicals, and combinations thereof; wherein X, Y and Z are pharmaceutically acceptable counterions or together are a pharmaceutically acceptable polydentate ligand, or are independently attached to one or more of the R groups and n is an integer from 0 to 3.

By an "analgesic amount" of the synthetic SOD catalysts herein is meant an amount that significantly prevents or alleviates pain in the human or lower animal being treated. At a certain level stimuli are perceived as painful, while below that level they are not. This level is referred to as the pain threshold. Healthy, normal subjects exhibit a normal pain threshold that can be quantified for a given stimulus. A normal healthy individual perceives a pin prick as painful, but does not perceive the movement of a joint within its normal range of motion as painful. An individual suffering from arthritis has a lowered pain threshold and will perceive such normal movement as painful. An individual suffering from sunburn has a lowered pain threshold and may perceive the touch of a finger to be as painful as a normal individual perceives a pin prick. Because these compounds operate to elevate a lowered pain threshold, they will be effective in the treatment of such pain, and an "analgesic amount" of synthetic SOD catalysts in the treatment methods provided here also means an amount that significantly elevates the pain threshold above its pre-treatment level or prevents the pain threshold from being lowered by a pathological condition. From the standpoint of the pharmacologist and pharmaceutical scientist, this can be measured prospectively using common animal models such as the phenylquinone writhing model, the rat tail flick (radiant heat) model, the carrageenan inflammation model, the Freund's adjuvant model, and other pain models well known to pharmacological science. From the standpoint of the clinician, this can be measured according to the subjective response of each patient to a unit dose of the compound, and subsequent doses can be titrated to achieve the desired level of analgesia within the therapeutic range of the compound employed.

By an "amount sufficient to prevent or reverse tolerance to opioids" is meant The dual administration of a superoxide dismutase catalyst together with an opioid such as morphine or fentanyl allows lower doses of the morphine or fentanyl to elicit its analgesic effects while limiting its side effects. Moreover, a superoxide dismutase catalyst can reverse opioid tolerance in patients who have already developed tolerance. Thus, the superoxide dismutase catalysts restore the analgesic effect lost during prolonged treatment with an opioid. These catalysts prevent or reverse the tolerance to opioids without many of the side effects of other compounds proposed for this purpose, such as clonidine and buprenorphine. And in contrast to other proposed compounds, such as inhibitors of inducible nitric oxide synthase, the superoxide dismutase catalysts themselves have potent analgesic effects that are useful in hyperalgesic conditions such as burns, arthritis and other inflammatory diseases, migraine, and pain associated with tumor infiltration and cancer therapy.

The compounds of this invention are also useful as adjuncts in the prevention and treatment of pain with opioid analgesics, nitric oxide donors or nonsteroidal anti-inflammatory compounds. In preferred embodiments, the superoxide dismutase catalyst is administered conjointly with the opioid, NO2 donor or NSAID compound. Administered in conjunction with an opioid, the superoxide dismutase catalyst potentiates the opioid and prevents development of tolerance and hyperalgesia. Administered after opioid tolerance, hyperalgesia and/or dependency have developed, the superoxide dismutase catalyst reverses the tolerance and hyperalgesia and reduces the symptoms of the withdrawal syndrome. Administered in conjunction with an NSAID compound or nitric oxide donor, the superoxide dismutase catalyst potentiates both the analgesia and the inflammatory action of the NSAID or NO2 donor. These drug moieties can also be linked to provide bifunctional compounds of the formula $A_n$-$Q_m$, wherein A is a superoxide dismutase catalyst moiety, Q is selected from nonsteroidal anti-inflammatory drug moieties, nitric oxide donor moieties and opioid analgesic drug moieties, and n and m are independently integers from 1 to 3. Depending upon the selection of A and Q, this can easily be done by substituting the NSAID or opioid moiety for one or more of counterion/ligands X, Y and Z in the preferred formula above. A simple approach to providing a combination containing a nitric oxide donor is to attach one or more nitrate or nitrite groups to the superoxide dismutase compound.

While not intending to be limited by theory, it is believed that the opioid withdrawal syndrome has many symptoms in common with the withdrawal syndromes associated with other addictive compounds and behaviors, including symptoms of withdrawal from cocaine, nicotine, and eating disorders such as anorexia and bulimia, especially the hyperreflexia and hyperalgesia associated with withdrawal. Accordingly, this invention also provides a method of preventing and treating symptoms of addition withdrawal, by administering to a patient in need of such treatment an amount of a superoxide dismutase catalyst that is safe and effective to prevent or reduce such symptoms.

A safe and effective amount of the compounds used in the practice of this invention is an amount that provides analgesia, thereby alleviating or preventing the pain being treated at a reasonable benefit/risk ratio as is intended with any medical treatment. In using the compounds for the reversal of opioid tolerance or reduction of withdrawal symptoms, these endpoints are used rather than analgesia. Obviously, the amount of catalyst used will vary with such factors as the particular condition that is being treated, the severity of the condition, the duration of the treatment, the physical condition of the patient, the nature of concurrent therapy (if any), the route of administration, the specific formulation and carrier employed, and the solubility and concentration of catalyst therein.

By "systemic administration" is meant the introduction of the catalyst or composition containing the catalyst into the tissues of the body, other than by topical application. Systemic administration thus includes, without limitation, oral and parenteral administration.

Depending upon the particular route of administration, and compatibility with the active compound chosen, a variety of pharmaceutically-acceptable carriers, well-known in the art, may be used. These include solid or liquid filler, diluents, hydrotropes, excipients, surface-active agents, and encapsulating substances. The amount of the carrier employed in conjunction with the catalyst is sufficient to provide a practical quantity of material per unit dose.

Pharmaceutically-acceptable carriers for systemic administration that may be incorporated into the compositions of this invention, include sugars, starches, cellulose and its derivatives, malt, gelatin, talc, calcium sulfate, vegetable oil, synthetic oils, polyols, alginic acid, phosphate buffer solutions, emulsifiers, isotonic saline, and pyrogen-free water.

The catalysts can be administered parenterally in combination with a pharmaceutically acceptable carrier such as corn oil, Cremophor EL or sterile, pyrogen-free water and a water-miscible solvent (e.g., ethyl alcohol) at a practical amount of the catalyst per dose. Preferably, the pharmaceutically-acceptable carrier, in compositions for parenteral administration, comprises at least about 90% by weight of the total composition. Parenteral administration can be by subcutaneous, intradermal, intramuscular, intrathecal, intraarticular or intravenous injection. The dosage by these modes of administration is usually in the range of from about 0.1 mg. to about 20 mg per day.

Various oral dosage forms can be used, including such solid forms as tablets, capsules, granules and bulk powders. These oral forms comprise a safe and effective amount, usually at least about 5%, and preferably from about 25% to about 50% of the catalyst. Tablets can be compressed, tablet triturates, enteric-coated, sugar-coated, film-coated or multiple compressed, containing suitable binders, lubricants, diluents, disintegrating agents, coloring agents, flavoring agents, preservatives, flow-inducing agents, and melting agents. Liquid oral dosage forms include aqueous solutions, emulsions, suspensions, solutions and/or suspensions reconstituted from noneffervescent granules and effervescent preparations reconstituted from effervescent granules, containing suitable solvents, preservatives, emulsifying agents, suspending agents, diluents, sweeteners, melting agents, coloring agents, and flavoring agents. Preferred carriers for oral administration include gelatin, propylene glycol, ethyl oleate, cottonseed oil and sesame oil. Specific examples of pharmaceutically-acceptable carriers and excipients that may be used to formulate oral dosage forms containing the catalysts used in this invention, are described in U.S. Pat. No. 3,903,297, Robert, issued Sep. 2, 1975, incorporated by reference herein. Techniques and compositions for making solid oral dosage forms are described in Marshall, "Solid Oral Dosage Forms," Modern Pharmaceutics, Vol. 7 (Banker and Rhodes, editors), 359–427 (1979), incorporated by reference herein.

By "pharmaceutically acceptable salts" is meant those salts that are safe for topical or systemic administration. These salts include the sodium, potassium, calcium, magnesium, and ammonium salts.

Carrageenan paw hyperalgesia testing

Sprague-Dawley rats (175–200 g, Harlan Sprague Dawley, Indianapolis, Ind., USA) were housed and cared for under the guidelines of the Institutional Animal Care and Use Committee. They received a subplantar injection of carrageenan (0.1 mL of a 1% suspension in 0.85% saline) into the right hind paw. At three hours post-carrageenan, when hyperalgesia is normally at a maximum, the test compound was administered intravenously at dosages of from 1–6 mg./kg. Hyperalgesia is assessed at thirty minutes to three hours post-administration of test compound.

EXAMPLE 1

SOD catalyst compounds were evaluated in the carrageenan hyperalgesia model described above. Results were as follows:

| Compound | Result |
| --- | --- |
| SC-71354 | No effect at tested dosages by intravenous injection* |
| SC-69604 | No effect at tested dosages by intravenous injection |
| SC-71449 | No effect at tested dosages by intravenous injection |
| SC-72325 | Inhibited hyperalgesia 64% at 30 minutes |
| SC-73770 | Inhibited hyperalgesia 72% at 30 minutes |

*Higher dosage levels and other routes of administration were not tested for any of the compounds.

EXAMPLE 2

Analgesia provided by intravenous SC-72325 was evaluated over time in the carrageenan model. Results are shown in FIG. 1.

EXAMPLE 3

Figure 2:
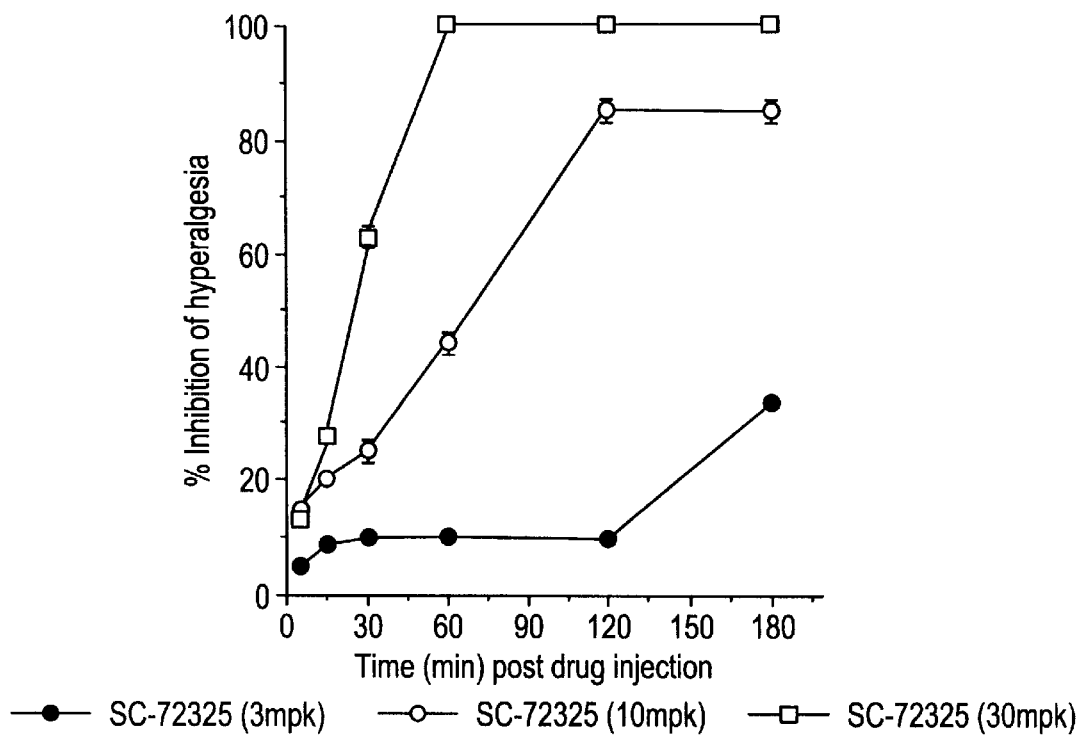
FIGS. 2 and 3 are graphs depicting the results of a study on inhibition of carrageenan-induced hyperalgesia by intramuscular injection of either SOD mimic compound SC-72325 (Example 157) or the nonsteroidal anti-inflammatory drug ketorolac.
Figure 3:
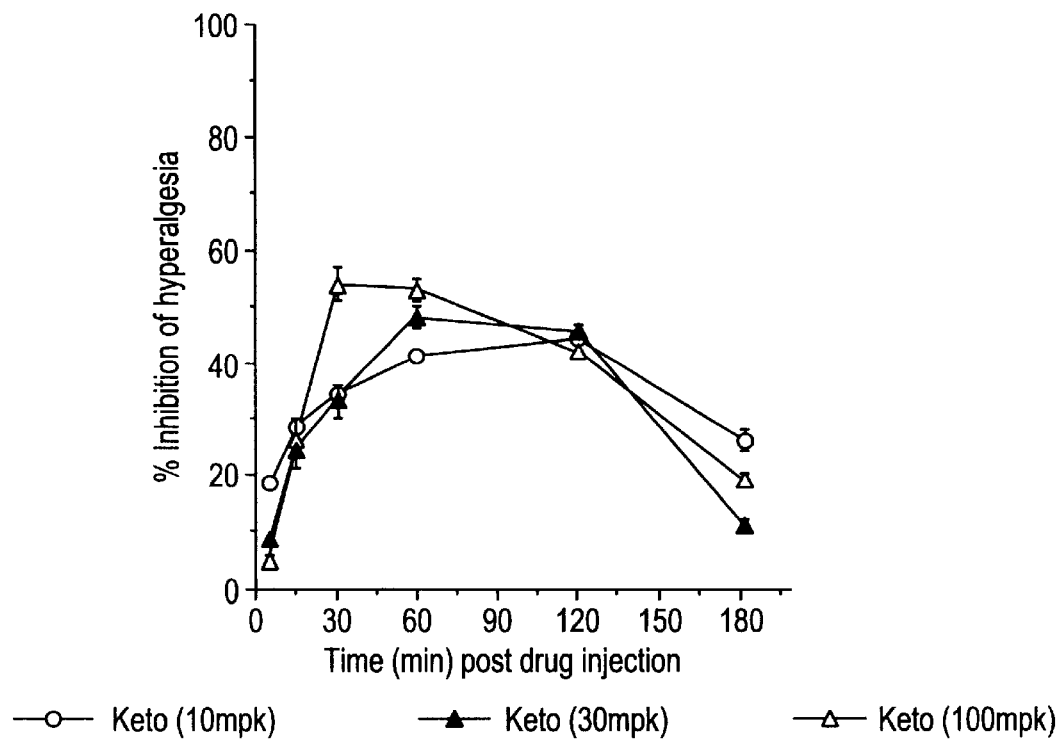

Analgesia provided by intramuscular injection of SC-72325 was evaluated over time in the carrageenan model in comparison to the anti-inflammatory drug ketorolac. Results are shown in FIGS. 2 and 3, respectively.

EXAMPLE 4

Figure 4:
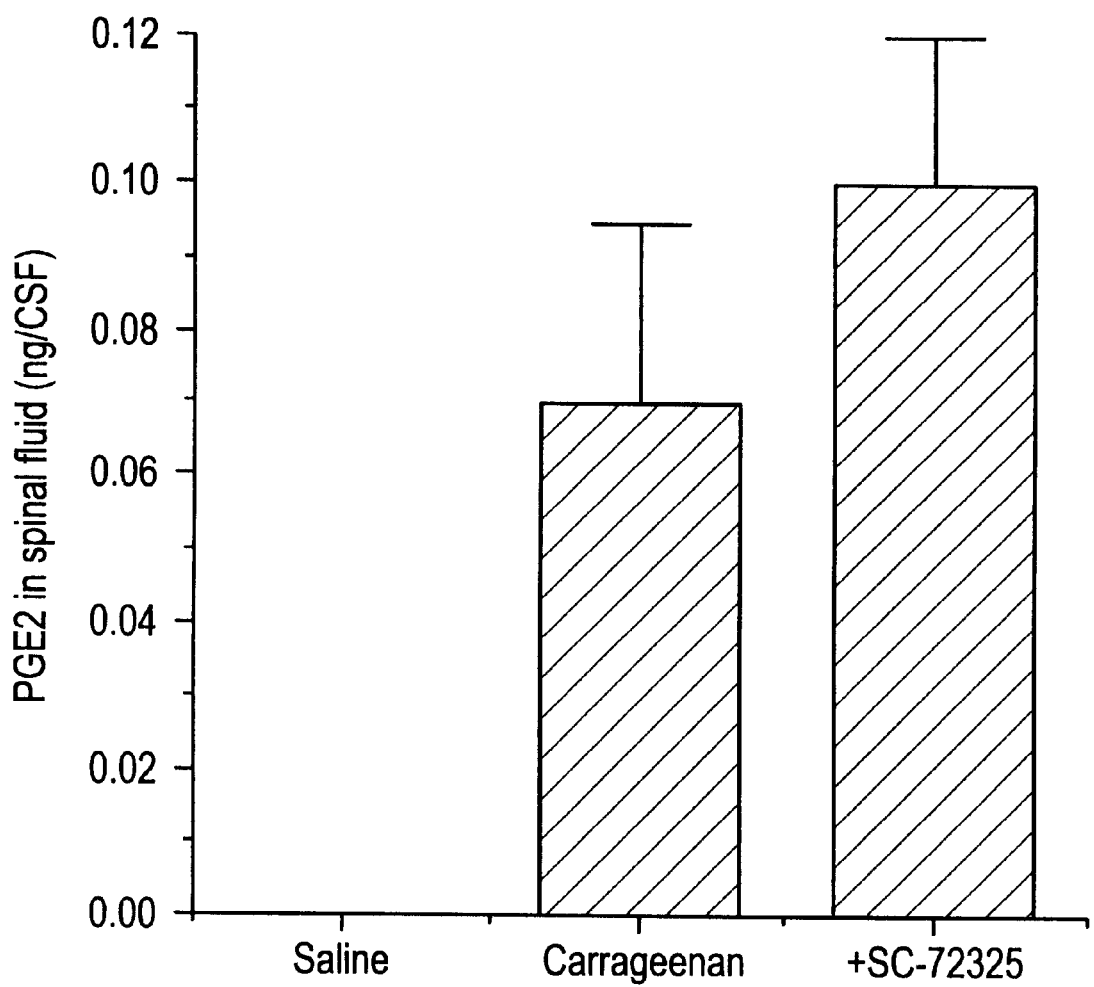
FIG. 4 is a graph depicting the results of a study comparing the effects of SC-72325 versus ketorolac on carrageenan-induced increase of PGE-2 in cerebrospinal fluid.
Figure 5:
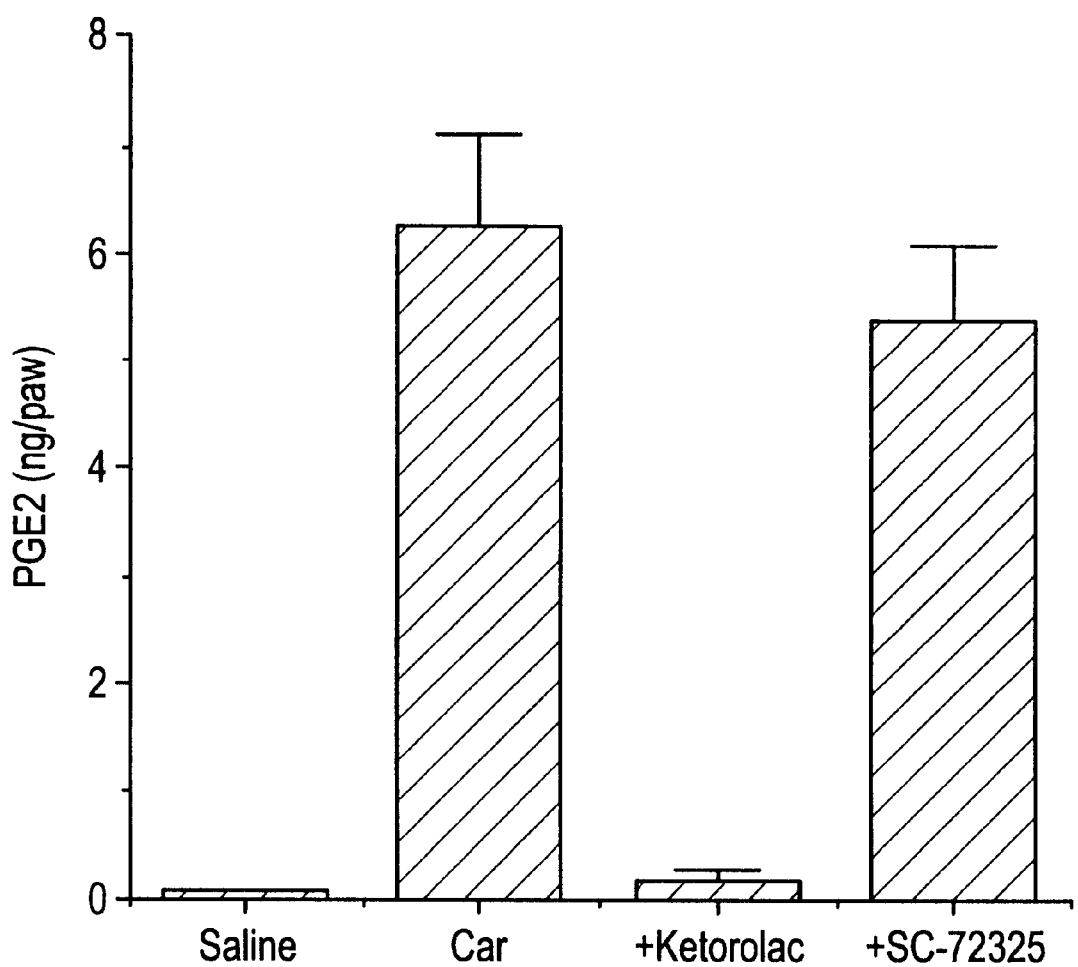
FIG. 5 is a graph depicting the results of a study comparing the effects of SC-72325 versus ketorolac on carrageenan-induced release of PGE-2 in paw exudate.

To determine whether the SOD catalyst compounds provide analgesia by some action on the prostaglandin-leukotriene system, release of prostaglandin PGE2 was measured in rat paw exudate from the carrageenan model as well as in spinal cord fluid. Saline was used as a non-inflamed control and the anti-inflammatory ketorolac was used as a positive anti-inflammatory control. Results are shown in FIGS. 4 and 5. SC-72325 did not significantly reduce release of PGE2 compared to the carrageenan-injected but untreated rats. Ketorolac treated rats had levels of PGE2 release similar to non-carrageenan injected animals.

EXAMPLE 5

Mice were treated twice a day with either saline (naïve) or morphine (s.c., 10 mg/kg) for a period of 4 days to induce tolerance. For comparison, a dose of 10 mg, or less than 0.15 mg/kg every 4 to 10 hours, is a morphine dosage routinely prescribed for the 70 kg. human adult with severe pain. On day 5, all mice received a subcutaneous challenge dose of 3 mg./kg morphine and the level of analgesia was measured 30 minutes later. Results are shown graphically in FIG. 6. Dose response measurements in normal mice have indicated that a challenge dose of 3 mg./kg. would elicit 90% analgesia in naive or non-tolerant mice when assessed by the standard hot plate test. In this example, mice that were treated with morphine for 4 days showed a decreased analgesic effect from morphine on day 5 when compared with the naïve mice. Tolerance to morphine was eliminated in mice that were treated with the superoxide dismutase catalyst SC-72325 administered intraperitoneally.

EXAMPLES 6–167

The following compounds were made for use as superoxide dismutase catalysts or as ligands for combination with transition metal ions for use as superoxide dismutase catalysts within the scope of the invention. The catalytic rate constant $k_{cat}$ is given for each compound. For $k_{cat}$ values marked with an asterisk, the $k_{cat}$ was measured at a pH of 8.1. For all other compounds the $k_{cat}$ was measured at pH 7.4. Compounds marked NT were made but not tested. The ligands of Examples 11, 101, 123–135 and 138–148 were not expected to have activity without the metal ion and most were not tested. However, as can be seen by comparison of Examples 148 and 149, insertion of the metal ion into the ligand forms a complex with good superoxide dismutase activity.

Example 6

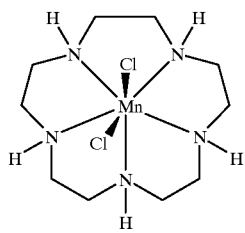

SC-52608

$4.13 \times 10^7$

Example 7

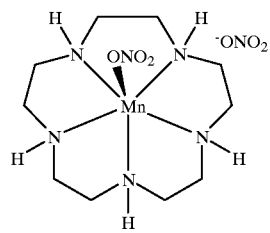

SC-53520

$2.30 \times 10^{7*}$

Example 8

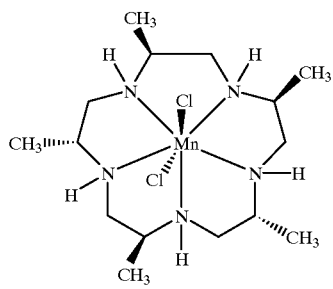

SC-55509

$2.60 \times 10^{7*}$

Example 9

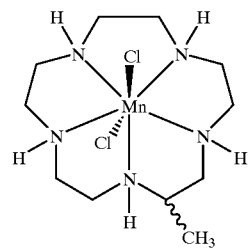

SC-52609

$2.60 \times 10^{7*}$

Example 10

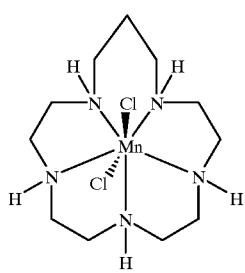

SC-52610

$0.110 \times 10^7$

Example 11

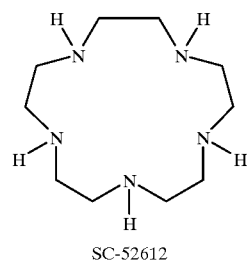

SC-52612

0.00

Example 12

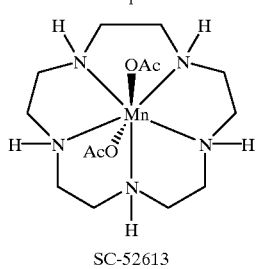

SC-52613

$1.85 \times 10^{7*}$

Example 13

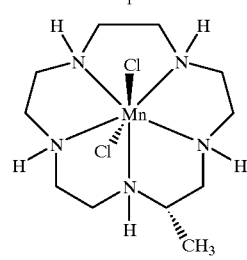

SC-52633

$2.39 \times 10^{7*}$

-continued
Example 14
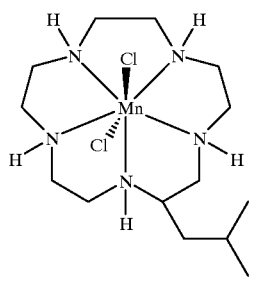
SC-52718
$1.91 \times 10^7$*
Example 15
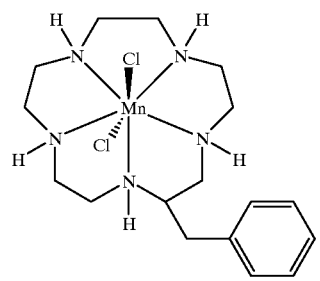
SC-52965
$7.21 \times 10^7$
Example 16
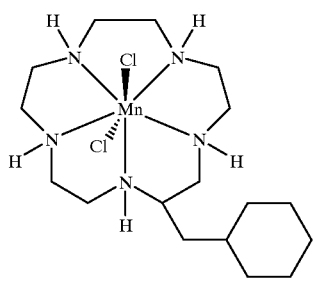
SC-53519
$2.07 \times 10^7$*
Example 17
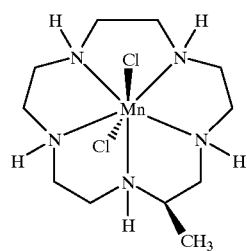
SC-53565
$6.65 \times 10^7$
Example 18
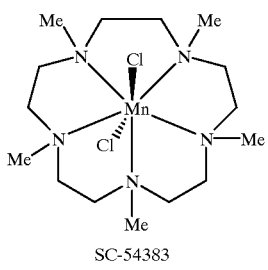
SC-54383
0
Example 19
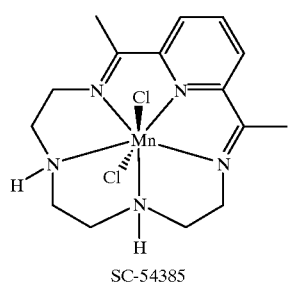
SC-54385
0
Example 20
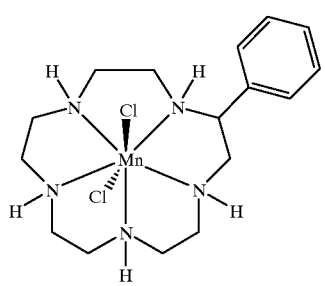
SC-54415
$1.76 \times 10^7$*
Example 21
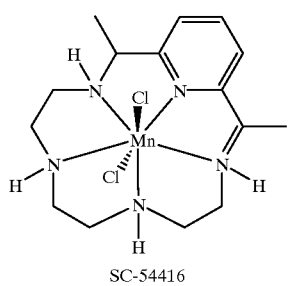
SC-54416
$1.00 \times 10^7$*

-continued
Example 22
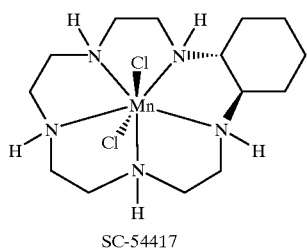
SC-54417
$9.09 \times 10^7$
Example 23
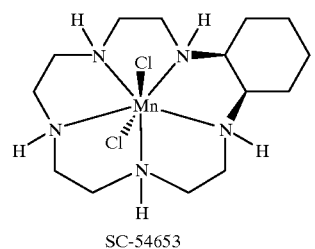
SC-54653
$1.86 \times 10^{7*}$
Example 24
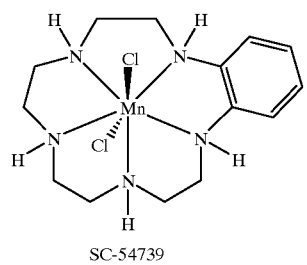
SC-54739
$4.09 \times 10^{7*}$
Example 25
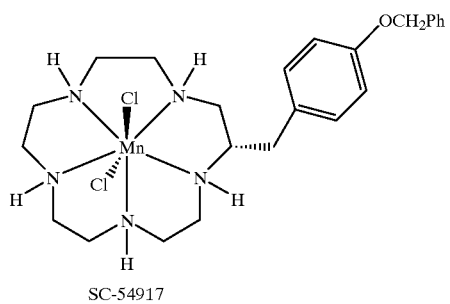
SC-54917
$1.70 \times 10^{7*}$
Example 26
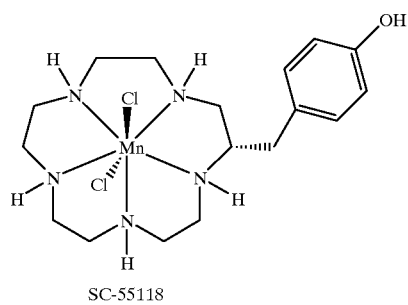
SC-55118
$1.82 \times 10^{7*}$
Example 27
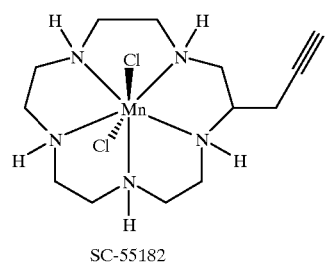
SC-55182
$1.75 \times 10^{7*}$
Example 28
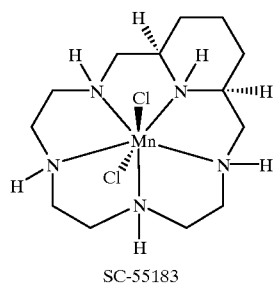
SC-55183
$0.680 \times 10^{7*}$
Example 29
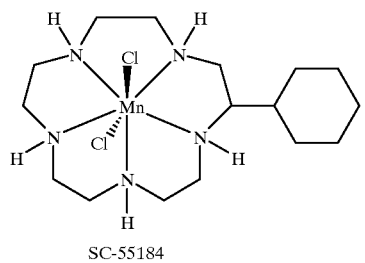
SC-55184
$1.42 \times 10^{7*}$ -continued
Example 30
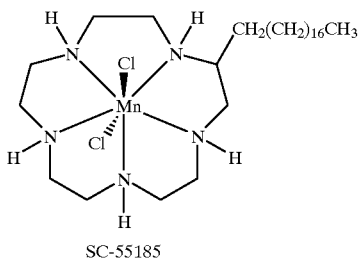
SC-55185
1.91 × 10⁷*
Example 31
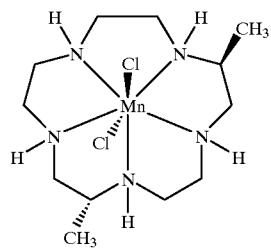
SC-55186
164 × 10⁷*
Example 32
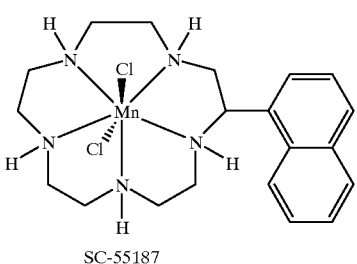
SC-55187
0.700 × 10⁷*
Example 33
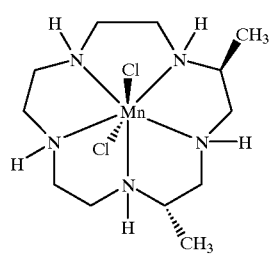
SC-55333
6.70 × 10⁷*
Example 34
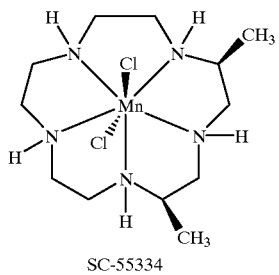
SC-55334
2.36 × 10⁷*
Example 35
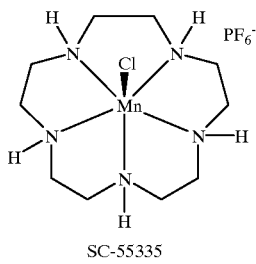
SC-55335
2.40 × 10⁷*
Example 36
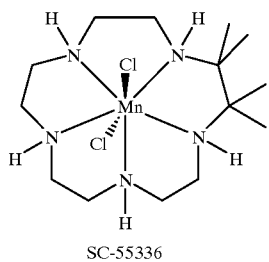
SC-55336
2.20 × 10⁷
Example 37
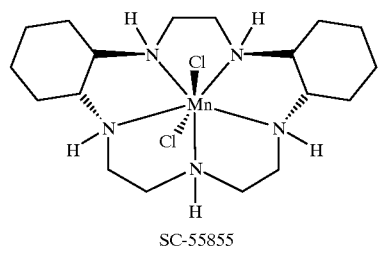
SC-55855
0.54 × 10⁷

-continued
Example 38
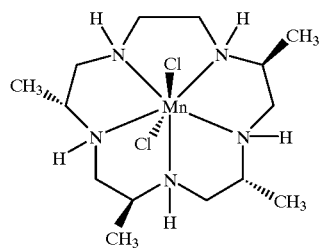
SC-55856
$5.37 \times 10^7$
Example 39
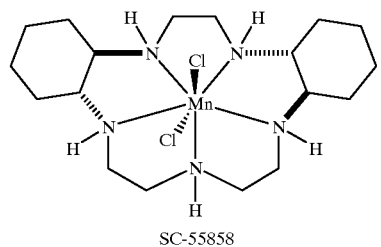
SC-55858
$12.08 \times 10^7$
Example 40
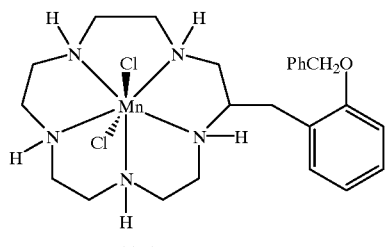
SC-55859
$1.34 \times 10^{7*}$
Example 41
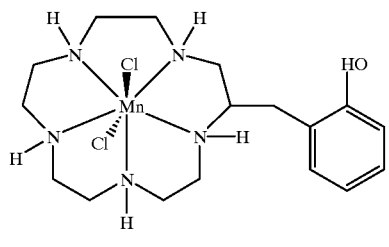
SC-55860
$6.99 \times 10^7$
Example 42
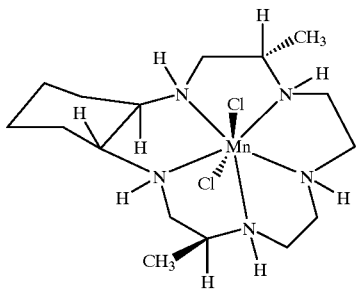
SC-56094
$10.70 \times 10^7$
Example 43
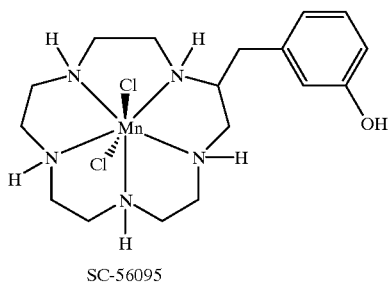
SC-56095
$1.88 \times 10^{7*}$
Example 44
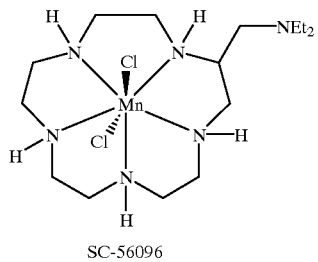
SC-56096
$5.87 \times 10^7$
Example 45
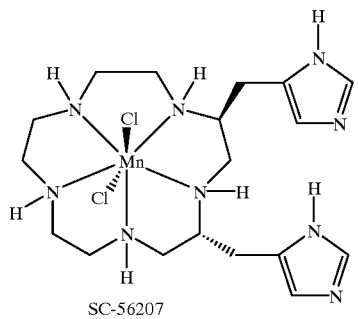
SC-56207
$2.00 \times 10^7$ -continued
Example 46
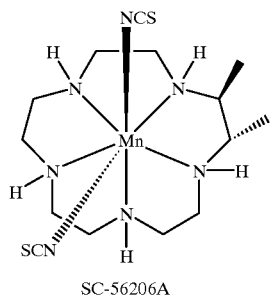
SC-56206A
NT
Example 47
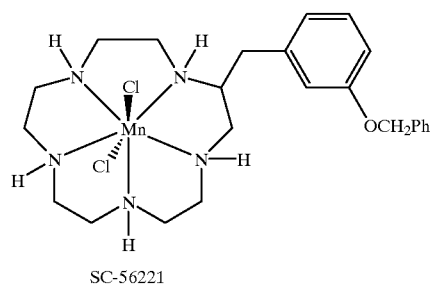
SC-56221
$1.91 \times 10^{7*}$
Example 48
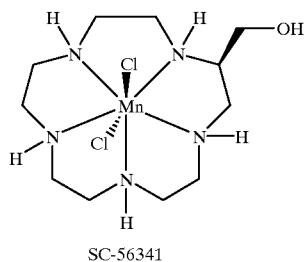
SC-56341
$4.59 \times 10^7$
Example 49
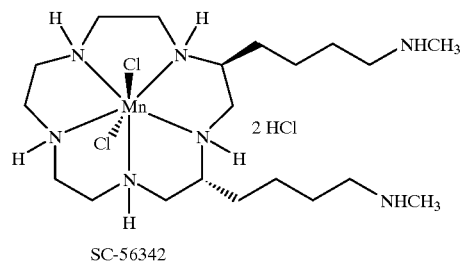
SC-56342
$5.95 \times 10^7$
Example 50
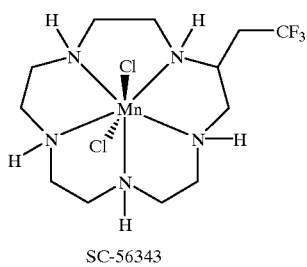
SC-56343
$2.77 \times 10^7$
Example 51
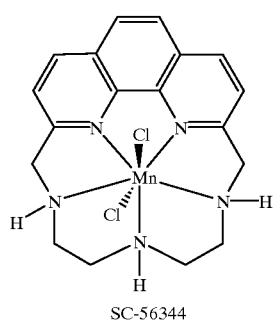
SC-56344
NT
Example 52
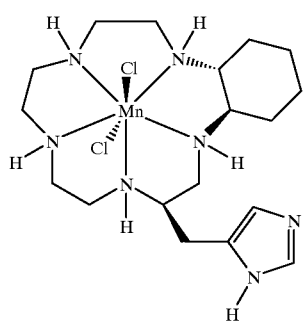
SC-56534
$2.95 \times 10^7$
Example 53
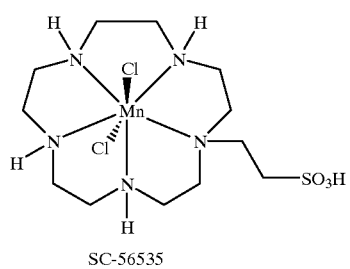
SC-56535
NT -continued
Example 54
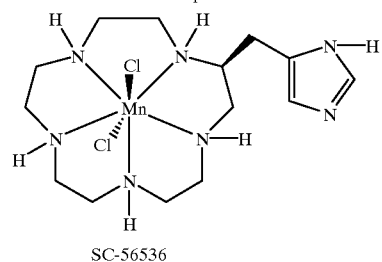
SC-56536
0.047 × 10⁷*
Example 55
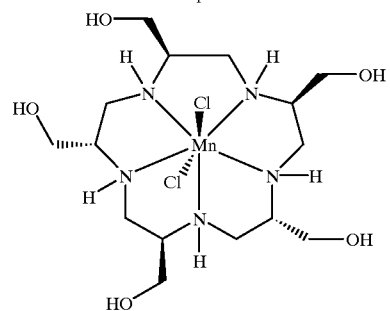
SC-56842
2.68 × 10⁷
Example 56
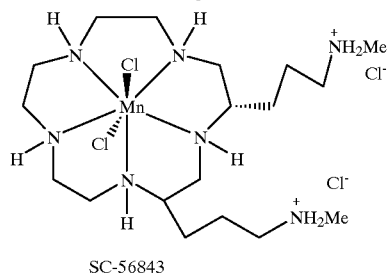
SC-56843
8.71 × 10⁷
Example 57
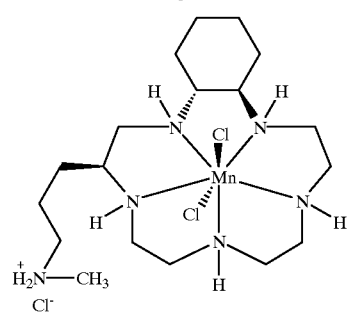
SC-57042
5.33 × 10⁷
Example 58
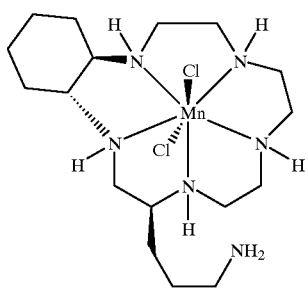
SC-57043
4.79 × 10⁷
Example 59
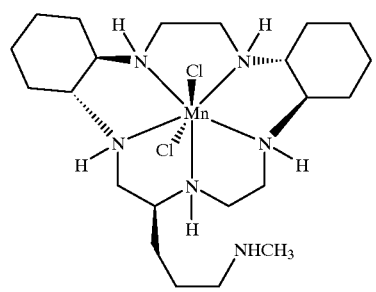
SC-57167
8.05 × 10⁷
Example 60
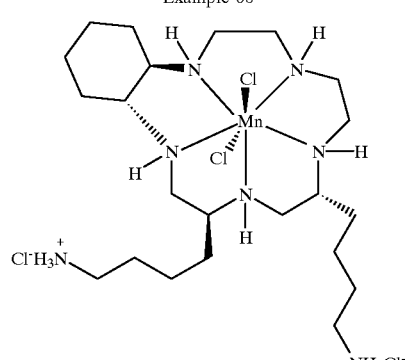
SC-57168
10.20 × 10⁷
Example 61
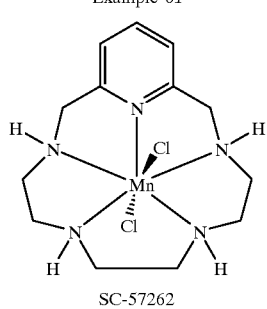
SC-57262
3.65 × 10⁷

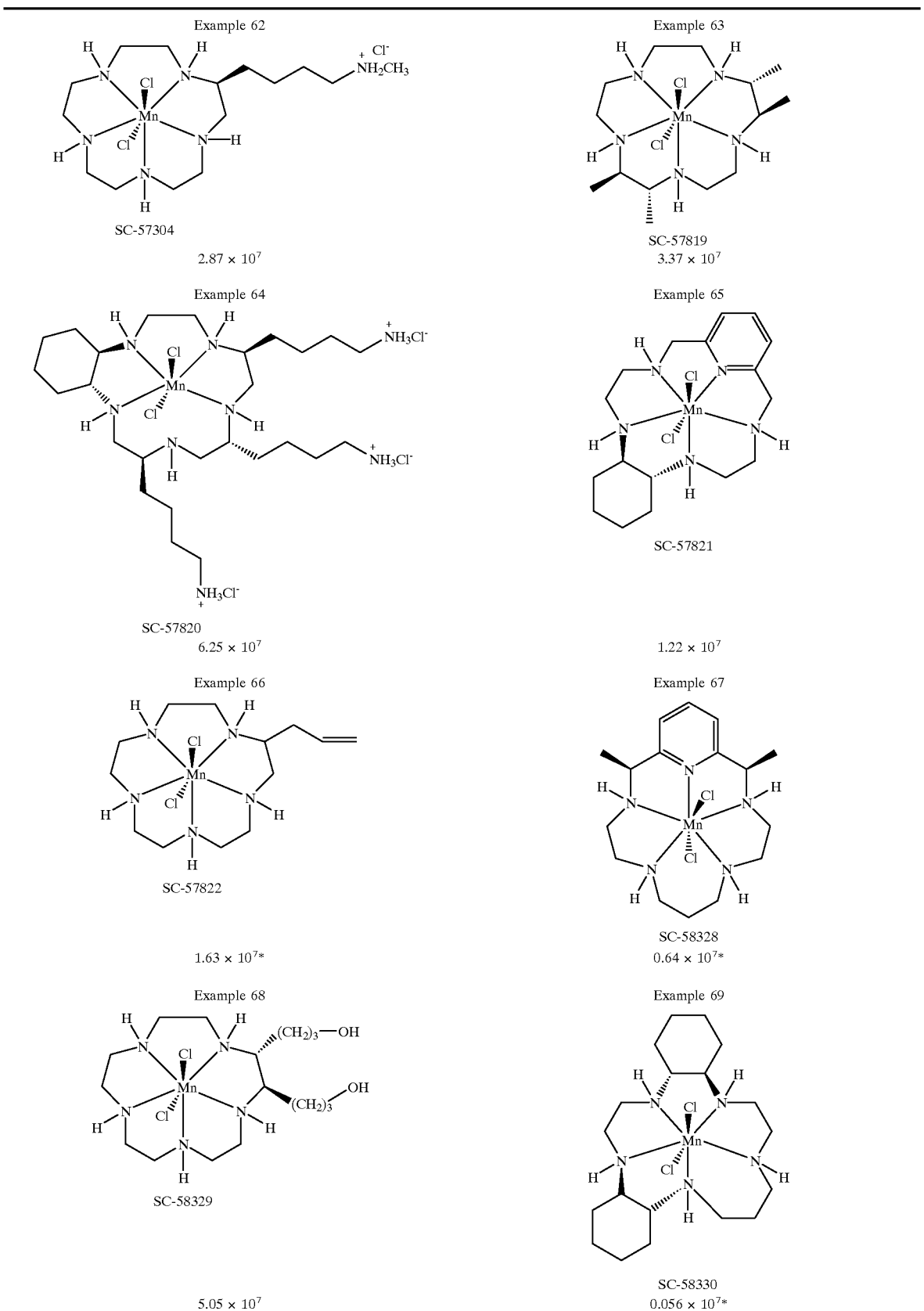

-continued
Example 70
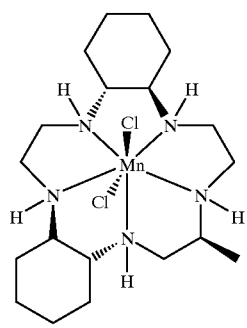
SC-58331
6.13 × 10⁷
Example 71
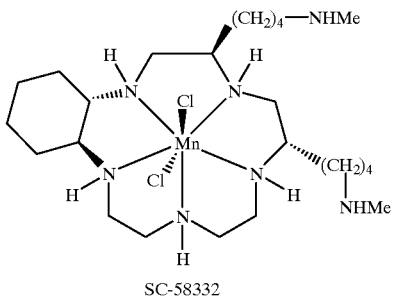
SC-58332
7.51 × 10⁷
Example 72
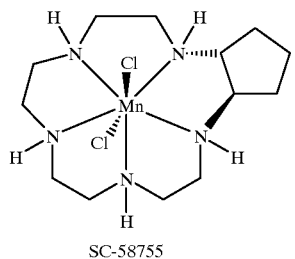
SC-58755
1.37 × 10⁷
Example 73
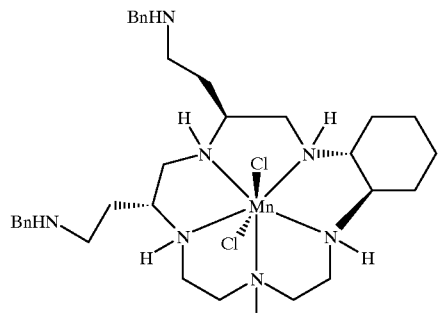
SC-59134
1.09 × 10⁷*
Example 74
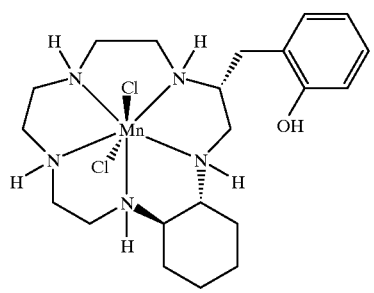
SC-59135
6.92 × 10⁷*
Example 75
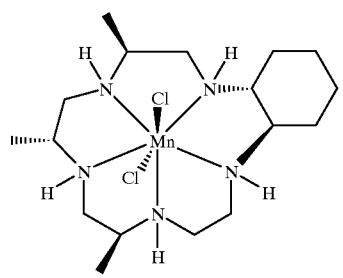
SC-59136
3.62 × 10⁷
Example 76
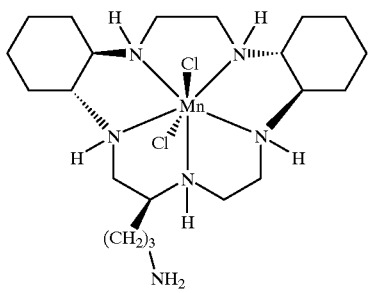
SC-59137
7.58 × 10⁷
Example 77
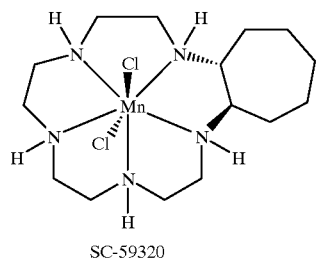
SC-59320
5.05 × 10⁷

Example 78
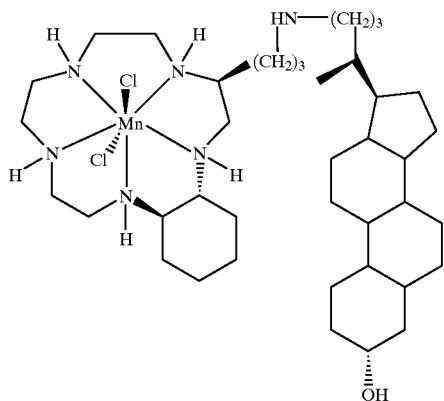
SC-59493
$2.41 \times 10^7$
Example 79
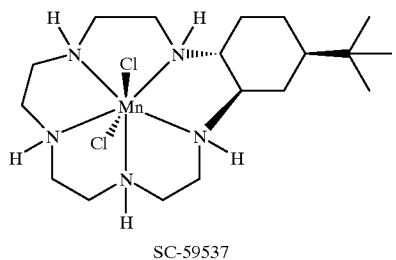
SC-59537
$7.23 \times 10^7$
Example 80
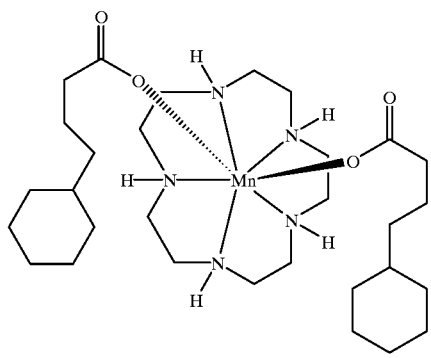
SC-59617
$1.74 \times 10^{7*}$
Example 81
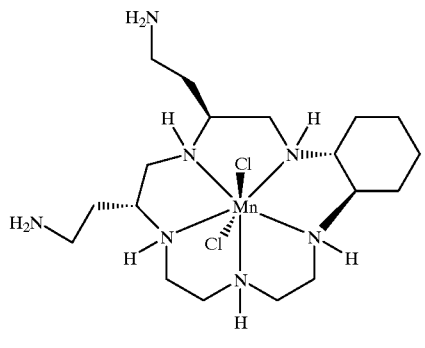
SC-59737
$2.48 \times 10^7$
Example 82
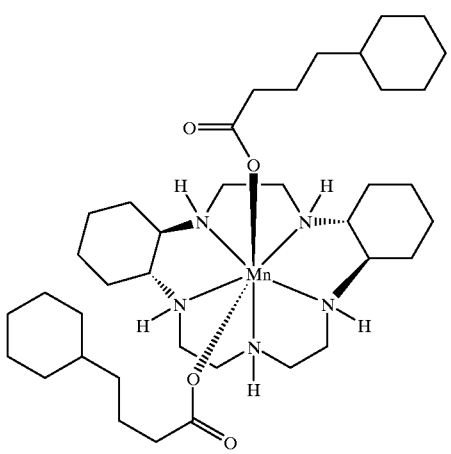
SC-60446
NT
Example 83
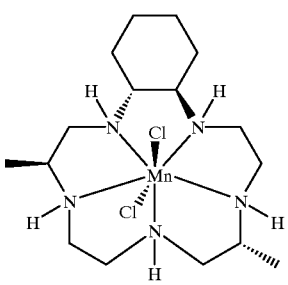
SC-60817
$9.09 \times 10^7$ -continued
Example 84
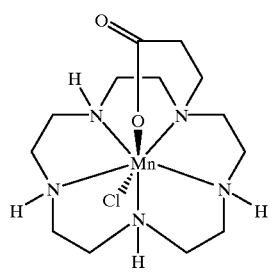
SC-60955
0.00
Example 85
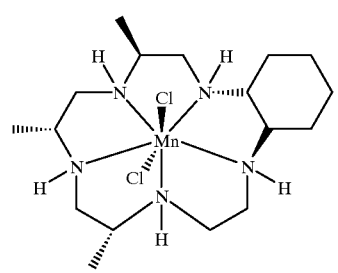
SC-63309
$9.56 \times 10^7$
Example 86
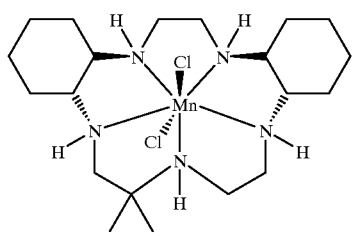
SC-63310
$0.3 \times 10^{7*}$
Example 87
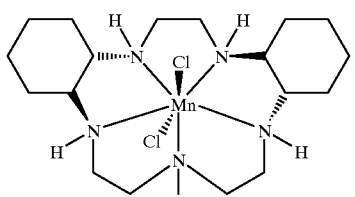
SC-63784
$12.60 \times 10^7$
Example 88
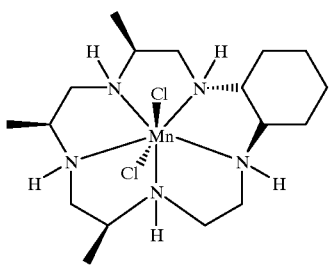
SC-64137
$10.84 \times 10^7$
Example 89
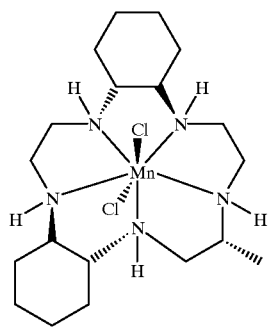
SC-65224
$15 \times 10^7$
Example 90
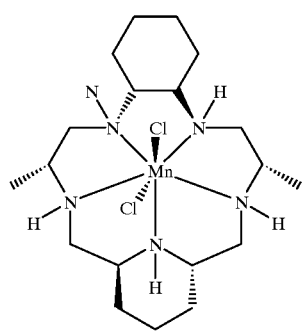
SC-65225
$2.96 \times 10^7$
Example 91
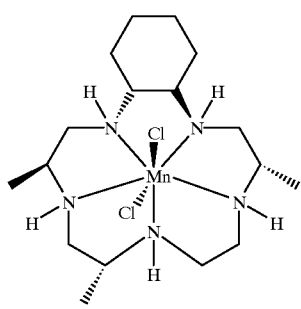
SC-65501
$8.48 \times 10^7$ -continued
Example 92
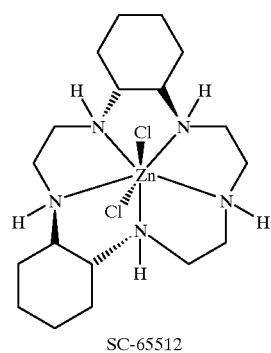
SC-65512
NT
Example 93
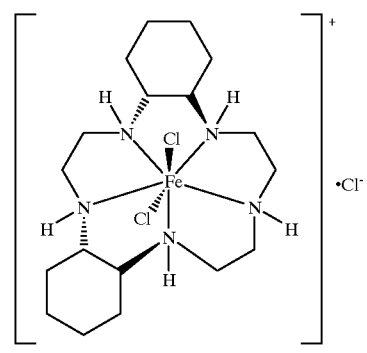
SC-65513
$3.29 \times 10^7$
Example 94
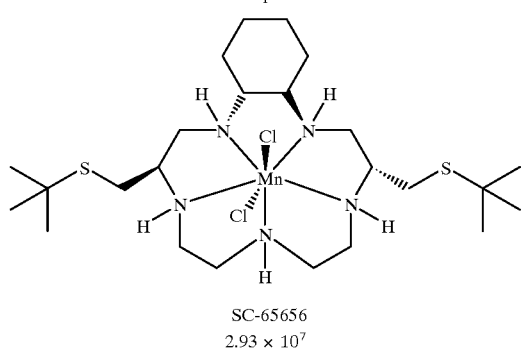
SC-65656
$2.93 \times 10^7$
Example 95
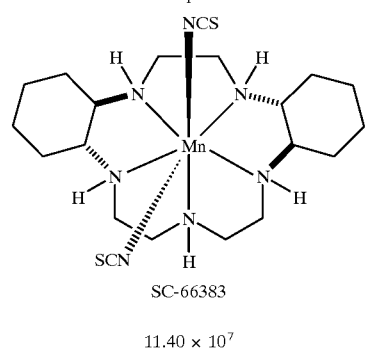
SC-66383
$11.40 \times 10^7$
Example 96
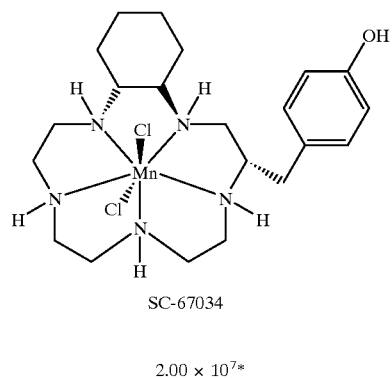
SC-67034
$2.00 \times 10^{7*}$
Example 97
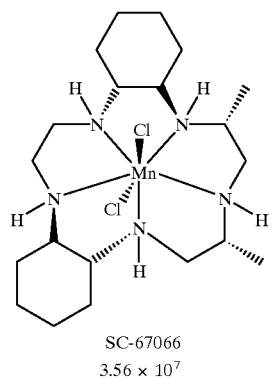
SC-67066
$3.56 \times 10^7$
Example 98
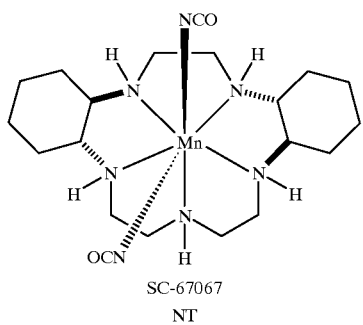
SC-67067
NT
Example 99
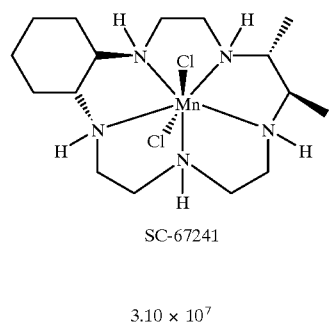
SC-67241
$3.10 \times 10^7$ -continued
Example 100
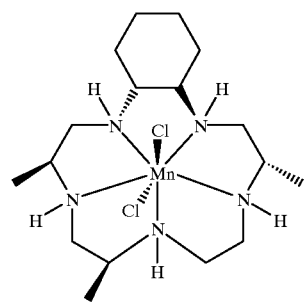
SC-67243
7.62 × 10⁷
Example 101
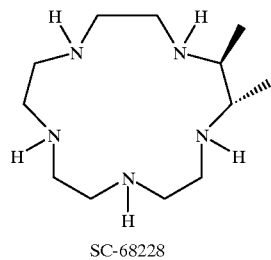
SC-68228
NT
Example 102
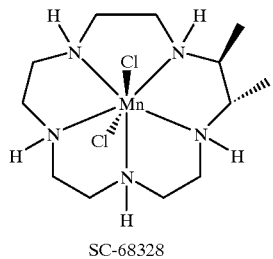
SC-68328
8.84 × 10⁷
Example 103
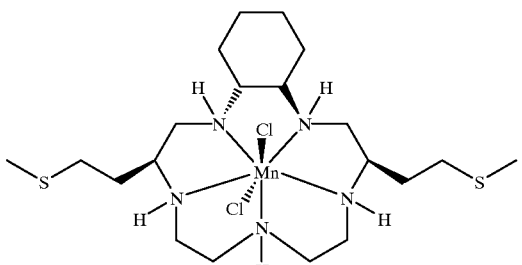
SC-68595
0.356 × 10⁷*
Example 104
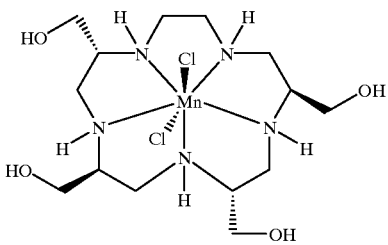
SC-69023
6.61 × 10⁷
Example 105
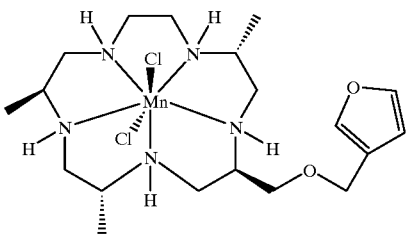
SC-69024
2.55 × 10⁷
Example 106
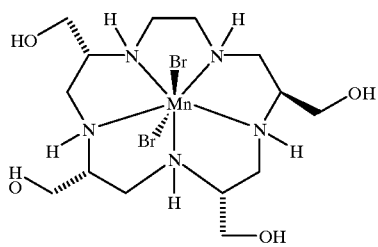
SC-69025
0.50 × 10⁷
Example 107
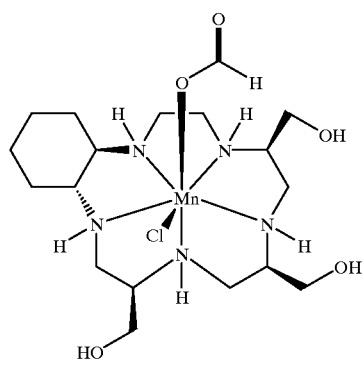
SC-69029
0.00

-continued
Example 108
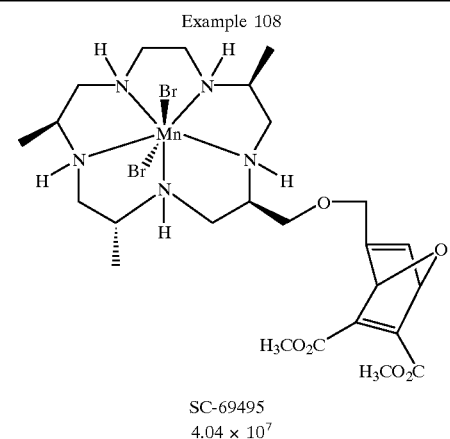
SC-69495
4.04 × 10⁷
Example 109
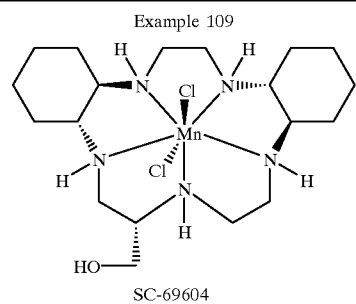
SC-69604
10.12 × 10⁷
Example 110
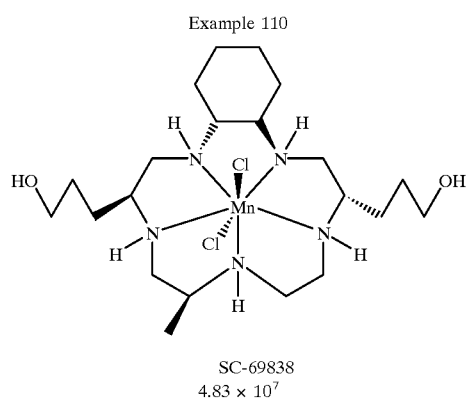
SC-69838
4.83 × 10⁷
Example 111
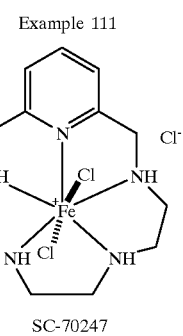
SC-70247
NT
Example 112
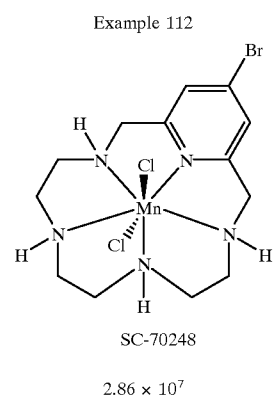
SC-70248
2.86 × 10⁷
Example 113
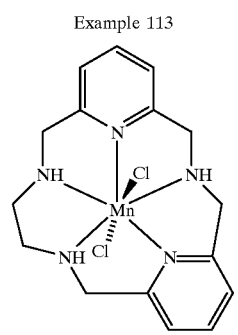
SC-70249
0.20 × 10⁷
Example 114
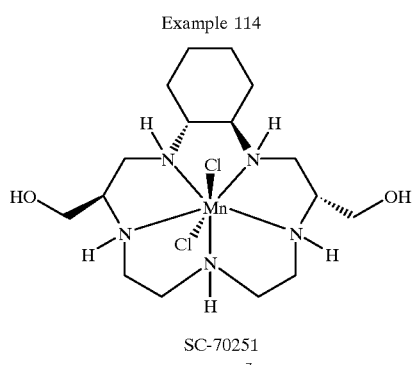
SC-70251
3.69 × 10⁷
Example 115
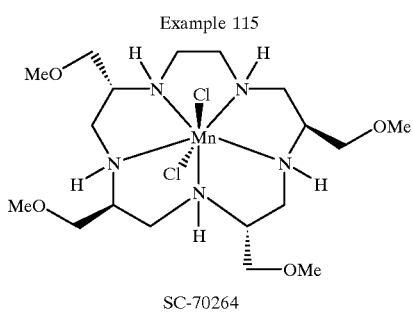
SC-70264
3.24 × 10⁷

-continued
Example 116
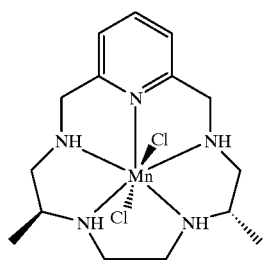
SC-70314
2.48 × 10$^7$
Example 117
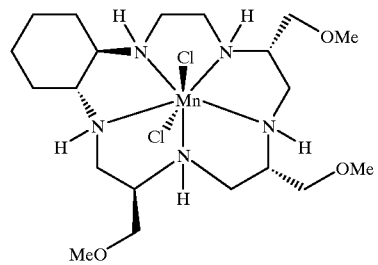
SC-70437
3.90 × 10$^7$
Example 118
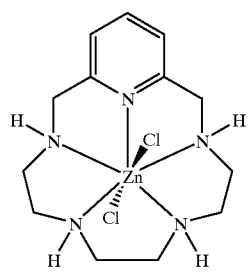
SC-70651
NT
Example 119
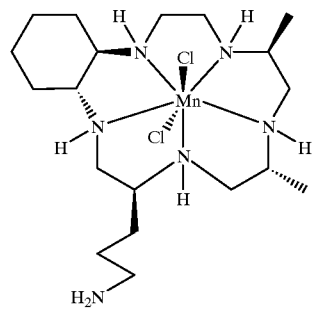
SC-70670
2.97 × 10$^7$
Example 120
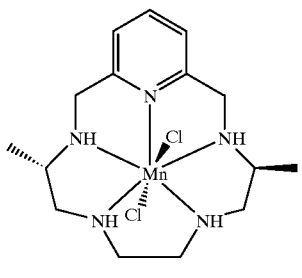
SC-70774
2.15 × 10$^{7*}$
Example 121
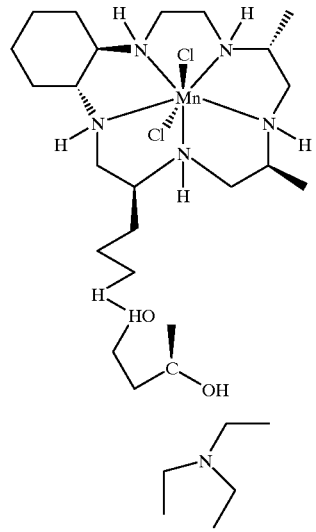
SC-70839
1.74 × 10$^{7*}$ -continued
Example 122
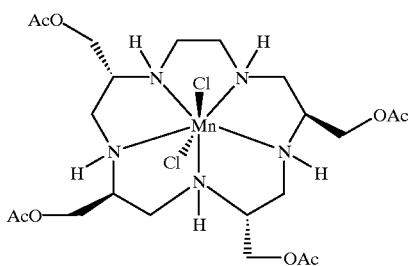
SC-71025
7.27 × 10⁷
Example 123
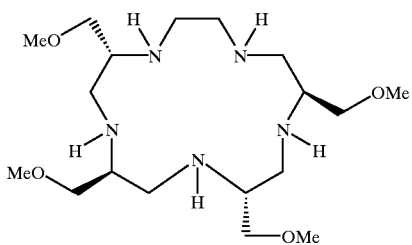
SC-71027
NT
Example 124
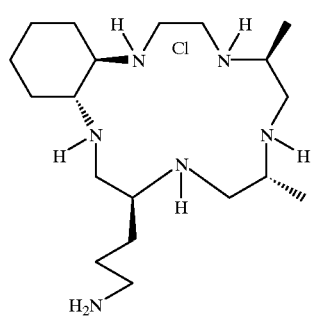
SC-71047
NT
Example 125
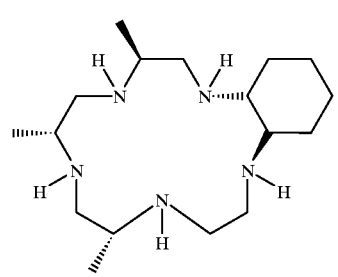
SC-71049
NT
Example 126
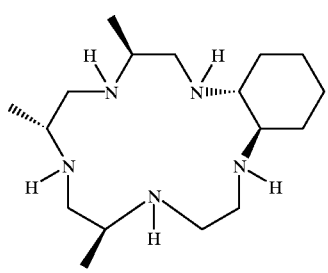
SC-71050
NT
Example 127
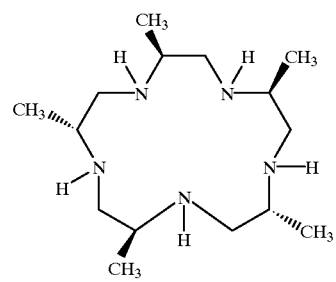
SC-71051
NT
Example 128
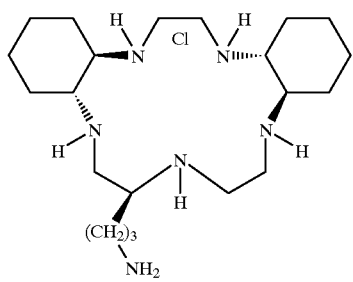
SC-71052
NT
Example 129
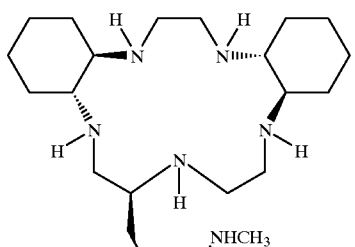
SC-71053
NT -continued
Example 130
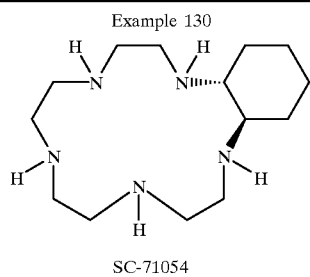
SC-71054
NT
Example 131
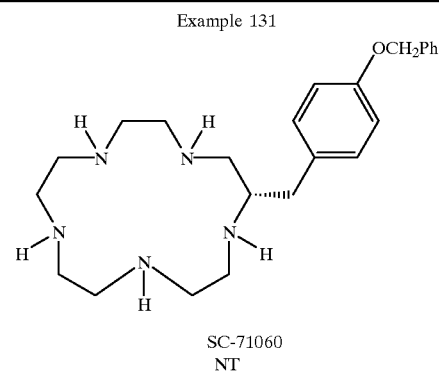
SC-71060
NT
Example 132
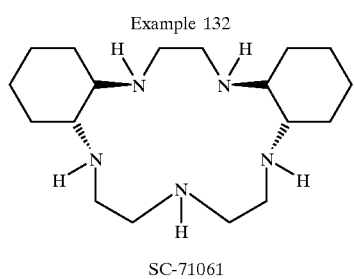
SC-71061
NT
Example 133
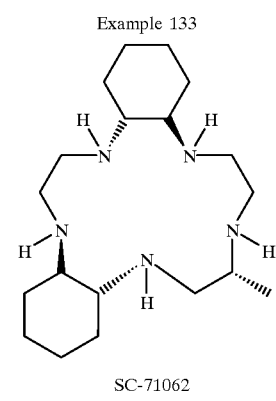
SC-71062
NT
Example 134
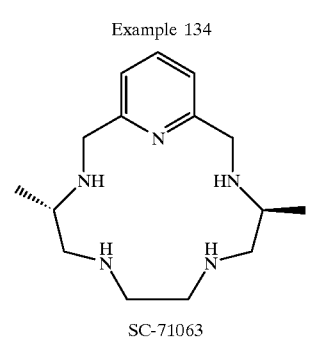
SC-71063
NT
Example 135
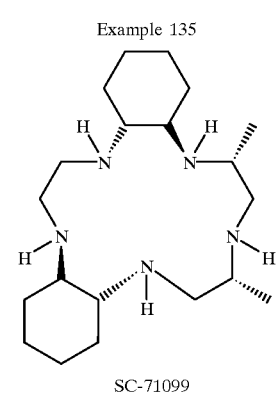
SC-71099
NT
Example 136
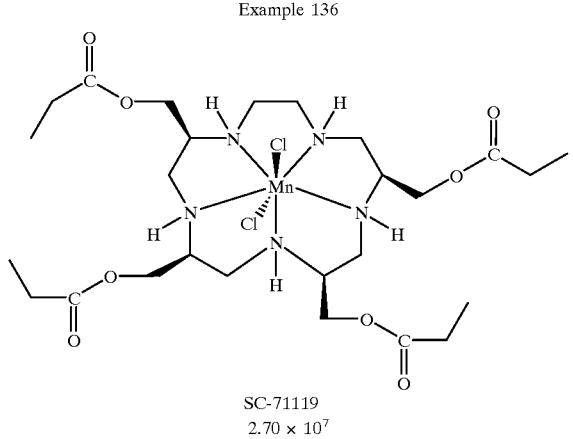
SC-71119
$2.70 \times 10^7$
Example 137
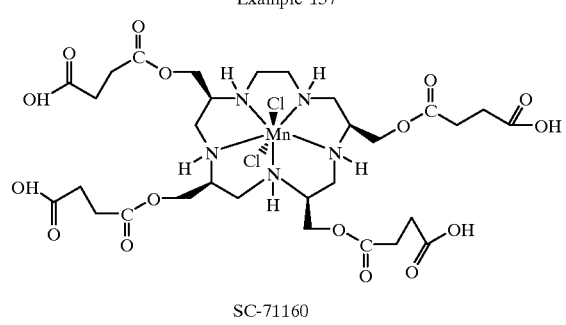
SC-71160
0.00

-continued
Example 138
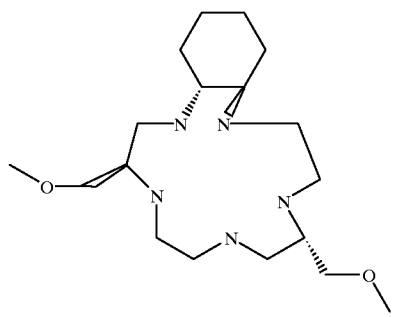
SC-71182
NT
Example 139
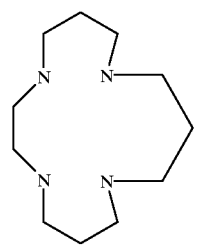
SC-71183
NT
Example 140
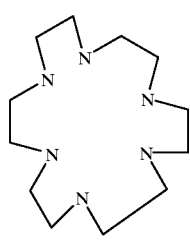
SC-71184
NT
Example 141
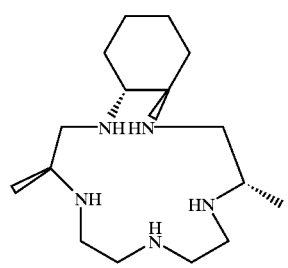
SC-71191
NT
Example 142
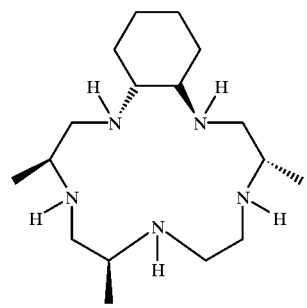
SC-71192
NT
Example 143
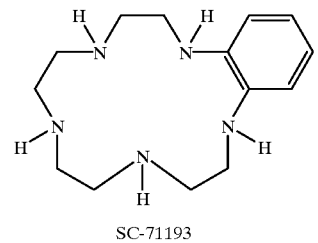
SC-71193
NT
Example 144
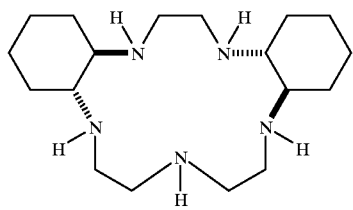
SC-71295
NT
Example 145
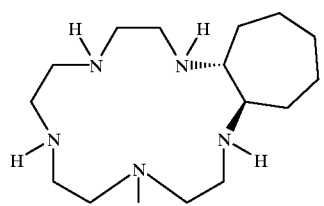
SC-71297
NT -continued
Example 146
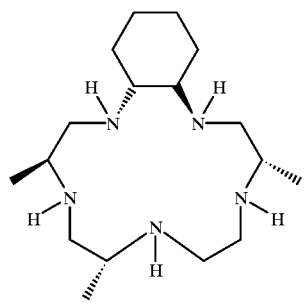
SC-71299
NT
Example 147
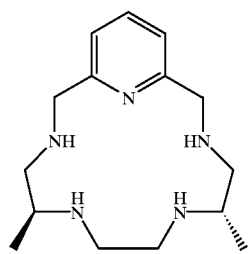
SC-71300
NT
Example 148
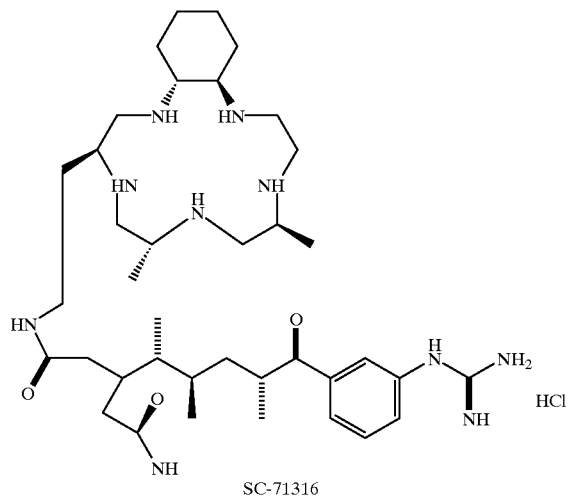
SC-71316
NT
Example 149
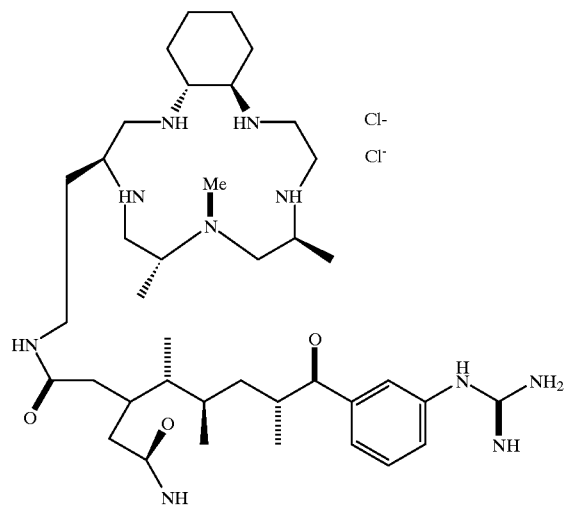
SC-71319
4.38 × 10$^7$
Example 150
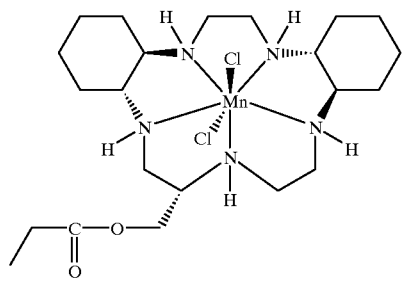
SC-71354
4.31 × 10$^7$*
Example 151
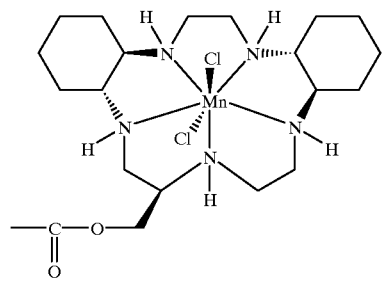
SC-71380
4.76 × 10$^7$ -continued
Example 152
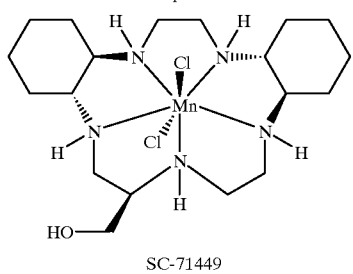
SC-71449
11.10 × 10^7
Example 153
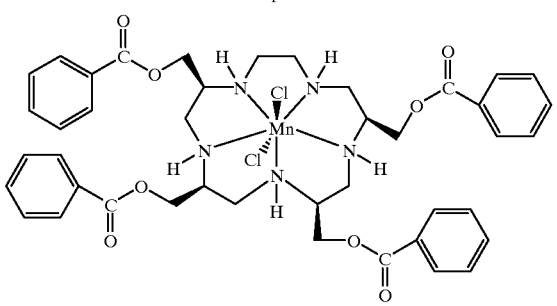
SC-71823
0.63 × 10^7
Example 154
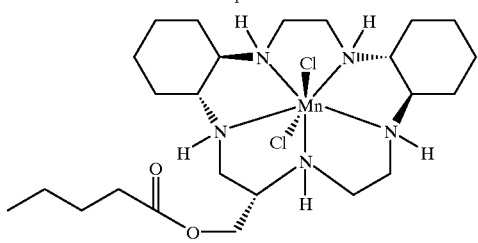
SC-71988
3.36 × 10^7
Example 155
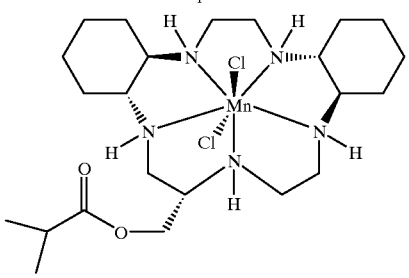
SC-72027
3.08 × 10^7
Example 156
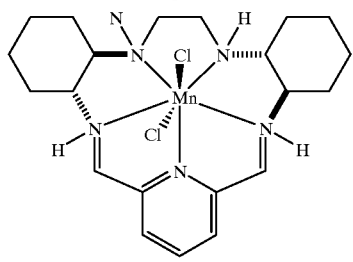
SC-72298
0.00
Example 157
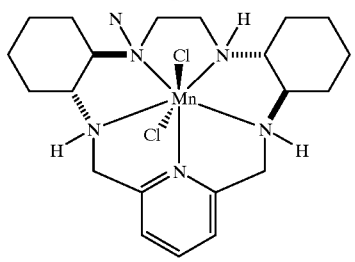
SC-72325
1.64 × 10^7
Example 158
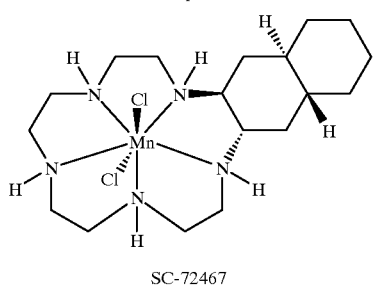
SC-72467
5.03 × 10^7
Example 159
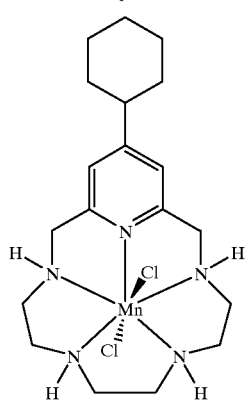
SC-72614
3.75 × 10^7

-continued
Example 160
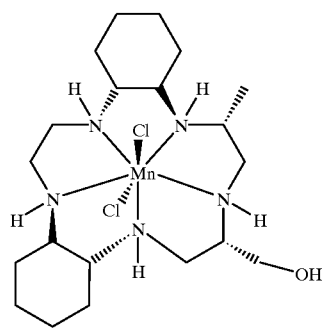
SC-72684
3.36 × 10⁷
Example 161
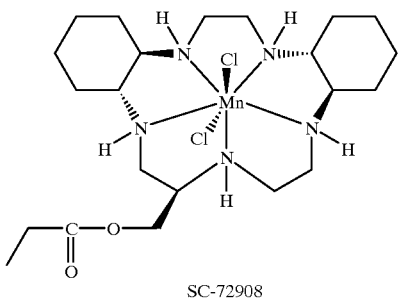
SC-72908
3.89 × 10⁷
Example 162
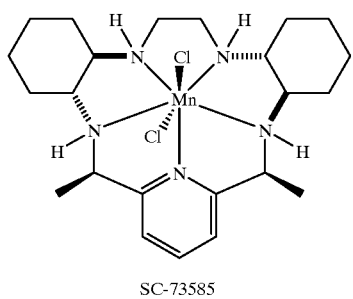
SC-73585
0.00
Example 163
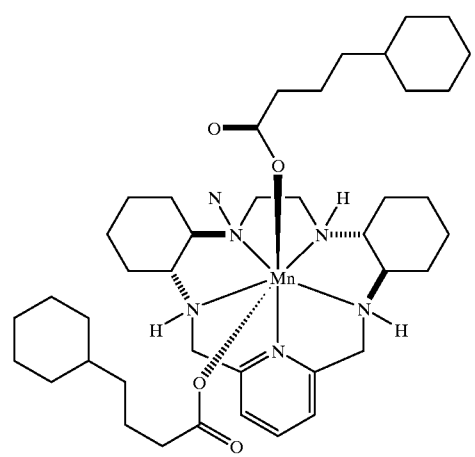
SC-73697
NT
Example 164
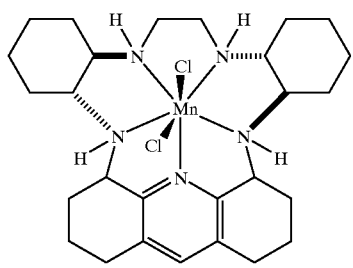
SC-73744
0.74 × 10⁷*
Example 165
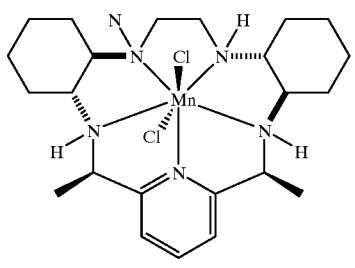
SC-73770
90.00 × 10⁷

-continued

Example 166

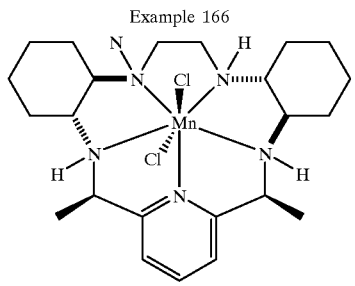

SC-73822
1.57 × 10⁷

From the foregoing description, one skilled in the art can easily identify the essential characteristics of the invention and can make various changes and modifications to the invention to adapt it to various usages and conditions without departing from the scope and spirit thereof.

What is claimed is:

1. A method of producing a central anti-hyperalgesic effect in a human patient in need of such treatment, comprising administering to the patient an anti-hyperalgesic amount of a functional synthetic catalyst for the dismutation of superoxide radicals, said catalyst being a complex of manganese and an organic ligand, said ligand comprising a nitrogen-containing macrocycle.

2. The method of claim 1, wherein the catalyst is selected from the group consisting of compounds of the formula:

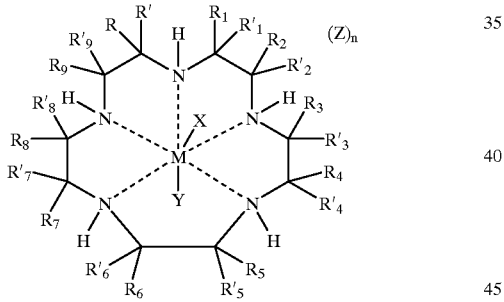

wherein M is manganese;

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently are selected from the group consisting of hydrogen and substituted or unsubstituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals;

or, $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, or $R_9$ or $R'_9$ and R or R' together with the carbon atoms to which they are attached independently form a substituted or unsubstituted, saturated, partially saturated or unsaturated cyclic or heterocyclic having 3 to 20 carbon atoms;

or, R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 2 to 20 carbon atoms, which may be an aromatic heterocycle wherein the hydrogen attached to the nitrogen which is both part of the heterocycle and the macrocycle and the R groups attached to the carbon atoms which are both part of the heterocycle and the macrocycle are absent;

or, R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a substituted or unsubstituted, saturated, partially saturated, or unsaturated cyclic or heterocyclic having 3 to 20 carbon atoms;

or, one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ attached to a different carbon atom in the macrocycle are bound to form a strap represented by the formula

—(CH₂)ₓ—M—(CH₂)𝓌—L—(CH₂)𝓏—J—(CH₂)𝓎— wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof;

or any combination of the above options for R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$;

and wherein X, Y and Z are pharmaceutically acceptable counter ions, or together are a pharmaceutically acceptable polydentate ligand and n is an integer from 0 to 3.

3. The method of claim 2, wherein at least one of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, or $R_9$ or $R'_9$ and R or R' together with the carbon atoms to which they are attached independently form a substituted or unsubstituted, saturated, partially saturated or unsaturated cyclic or heterocyclic having 3 to 20 carbon atoms.

4. The method of claim 3, wherein at least one of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, or $R_9$ or $R'_9$ and R or R' together with the carbon atoms to which they are attached independently form a saturated cyclic having 6 carbon atoms.

5. The method of claim 2, wherein R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing aromatic heterocycle having 2 to 20 carbon atoms, wherein the hydrogen attached to the nitrogen which is both part of the heterocycle and the macrocycle and the R groups attached to the carbon atoms which are both part of the heterocycle and the macrocycle are absent.

6. The method of claim 5, wherein the substituted or unsubstituted nitrogen containing aromatic heterocycle has 5 carbon atoms.

7. The method of claim 6, wherein at least one other of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, or $R_9$ or $R'_9$ and R or R' together with the carbon atoms to which they are attached independently form a saturated cyclic having 6 carbon atoms.

8. A method of producing a central anti-hyperalgesic effect in a lower mammal patient in need of such treatment, comprising administering to the patient an anti-hyperalgesic amount of a functional synthetic catalyst for the dismutation of superoxide radicals, said catalyst being a complex of manganese and an organic ligand, said ligand comprising a nitrogen-containing macrocycle.

9. The method of claim 8, wherein the catalyst is selected from the group consisting of compounds of the formula:

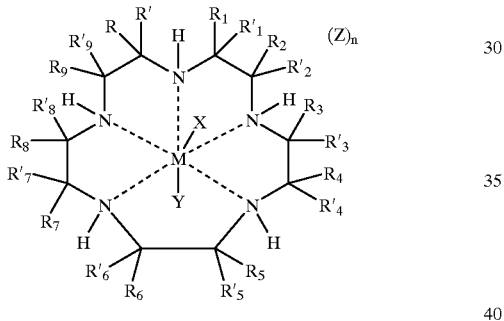

wherein M is manganese;

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently are selected from the group consisting of hydrogen and substituted or unsubstituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals;

or, $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, or $R_9$ or $R'_9$ and R or R' together with the carbon atoms to which they are attached independently form a substituted or unsubstituted, saturated, partially saturated or unsaturated cyclic or heterocyclic having 3 to 20 carbon atoms;

or, R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 2 to 20 carbon atoms, which may be an aromatic heterocycle wherein the hydrogen attached to the nitrogen which is both part of the heterocycle and the macrocycle and the R groups attached to the carbon atoms which are both part of the heterocycle and the macrocycle are absent;

or, R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a substituted or unsubstituted, saturated, partially saturated, or unsaturated cyclic or heterocyclic having 3 to 20 carbon atoms;

or, one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ attached to a different carbon atom in the macrocycle are bound to form a strap represented by the formula

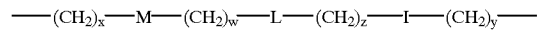

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof;

or any combination of the above options for R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$;

and wherein X, Y and Z are pharmaceutically acceptable counter ions, or together are a pharmaceutically acceptable polydentate ligand and n is an integer from 0 to 3.

* * * * *